(12) United States Patent
Woods et al.

(10) Patent No.: US 6,699,696 B2
(45) Date of Patent: Mar. 2, 2004

(54) GENETICALLY MODIFIED CYANOBACTERIA FOR THE PRODUCTION OF ETHANOL, THE CONSTRUCTS AND METHOD THEREOF

(75) Inventors: Robert Paul Woods, Markham (CA); John Robert Coleman, Toronto (CA); Ming De Deng, North York (CA)

(73) Assignee: Enol Energy Inc., Toronto (CA)

( * ) Notice: Subject to any disclaimer, the term of this patent is extended or adjusted under 35 U.S.C. 154(b) by 153 days.

(21) Appl. No.: 09/861,819

(22) Filed: May 21, 2001

(65) Prior Publication Data

US 2002/0042111 A1 Apr. 11, 2002

Related U.S. Application Data

(60) Division of application No. 09/026,845, filed on Feb. 20, 1998, now Pat. No. 6,306,639, which is a continuation-in-part of application No. 08/801,331, filed on Feb. 19, 1997, now abandoned.

(51) Int. Cl.[7] ................................................. C12P 7/06
(52) U.S. Cl. .................... 435/161; 435/41; 435/155; 435/252.3; 536/23.1; 536/23.2; 536/24.1
(58) Field of Search .......................... 435/41, 155, 161, 435/252.3; 536/23.1, 23.2, 24.1

(56) References Cited

U.S. PATENT DOCUMENTS

| | | |
|---|---|---|
| 4,778,759 A | 10/1988 | Szalay et al. |
| 5,000,000 A | 3/1991 | Ingram et al. |
| 5,028,539 A | 7/1991 | Ingram et al. |
| 5,270,175 A | 12/1993 | Moll |

FOREIGN PATENT DOCUMENTS

| | | |
|---|---|---|
| JP | 07 079782 | 5/1995 |
| WO | WO 9527064 | 12/1995 |

OTHER PUBLICATIONS

Soltes–Rak, E. et al., The Genomic Region of RbcLS in Synechococcus sp. PCC 7642 Contains Genes Involved in the ability to Grow under Low CO2 Concentration and in Chlorophyll Biosynthesis 1, Appl. Env. Micro., vol. 59, No. 8, pp. 2404–2410.

Ronen–Tarazi, M. et al., Effect of Promoter Modification on Mosquitocidal cryIVB Gene Expression in Synechococcus sp. Strn PCC 7942, Plant Physiol., vol. 108, pp. 1461–1469.

Gruber et al., Cur. Micro., vol. 22, pp. 15–19.

*Primary Examiner*—Ponnathapu Achutamurthy
*Assistant Examiner*—Christian L Fronda
(74) *Attorney, Agent, or Firm*—Michael Best & Friedrich LLP

(57) ABSTRACT

The invention provides a genetically modified Cyanobacteria having a construct comprising DNA fragments encoding pyruvate decarboxylase (pdc) and alcohol dehydrogenase (adh) enzymes obtained from the *Zymomonas mobilis* plasmid pLOI295. The Cyanobacteria are capable of producing ethanol in recoverable quantities of at least 1.7 μmol ethanol per mg of chlorophyll per hour.

10 Claims, 22 Drawing Sheets

Figure 9 (1)

```
LOCUS       ZMOPDC      1905 bp ds-DNA       BCT      30-JUN-1987
DEFINITION  Zymomonas mobilis pyruvate decarboxylase (pdc) gene, complete cds.
ACCESSION   M15393
KEYWORDS    decarboxylase; pyruvate decarboxylase.
SOURCE      Z.mobilis (strain CP4) DNA, clone pLOI275, subclone pLOI276.
  ORGANISM  Zymomonas mobilis
            Prokaryotae; Facultative anaerobic gram-negative rods.
REFERENCE   1 (bases 1 to 1905)
  AUTHORS   Conway,T., Osman,Y.A., Konnan,J.I., Hoffmann,E.M. and Ingram,L.O.
  TITLE     Promoter and nucleotide sequences of the Zymomonas mobilis pyruvate
            decarboxylase
  JOURNAL   J. Bacteriol. 169, 949-954 (1987)
  MEDLINE   87137309
COMMENT     Computer-readable copy of sequence in [1] kindly provided by
            T.Conway (27-APR-1987).
            There is a potential ribosome binding region at bases 189-192.

NCBI gi: 155597
FEATURES            Location/Qualifiers
     source         1..1905
                    /organism="Zymomonas mobilis"
     mRNA           153..>1878
                    /note="pdc mRNA"
     CDS            199..1878
                    /note="pyruvate decarboxylase (E.C 4.1.1.1); NCBI gi:
                    155598"
                    /codon_start=1
```

/translation="MSYTVGTYLAALVQIGLKHHFAVAGDYNLVLLDNLLLNKNMEQV

YCCNELNCGFSAEGYARAKADAAAVVTYSVGALSAFDAIGGAYAENLPVILISGAPNN

NDHAAGHVLHHALGKTDYHYQLEMAKNITAAAEAIYTPEEAPAKIDHVIKTALREKKP

VYLEIACNIASMPCAAPGPASALFNDEASDEASLNAAVEETLKFIANRDKVAVLVGSK

LRAAGAEEAAVKFADALGGAVATMAAAKSFFQKKTALHRYLMGEVSYPGVEKTMKE
AD

AVIALAPVFNDYSTTGWTDIPDPKKLVLAEPRSVVVNGVRFPSVHLKDYLTRLAQKVS

KKTGALDFFKSLNAGELKKAAPADPSAPLVNAEIARQVEALLTPNTTVIAETGDSWFN

AQRMKLPNGARVEYEMQWGHIGWSVPAAFGYAVGAPERRNILMVGDGSFQLTAQEV
AQ

Figure 9 (2)

MVRLKLPVIIFLINNYGYTIEVMIHDGPYNNIKNWDYAGLMEVFNGNGGYDSGAGKGL

KAKTGGELAEAIKVALANTDGPTLIECFIGREDCTEELVKWGKRVAARQQP"
BASE COUNT    467 a    489 c    473 g    476 t
ORIGIN    106 bp upstream of DraI site.
```
   1 tatcgctcat gatcgcgaca tgttctgata ttttcctcta aaaaagataa aaagtctttt
  61 cgcttcggca gaagaggttc atcatgaaca aaaattcggc attttaaaa atgcctatag
 121 ctaaatccgg aacgacactt tagaggtttc tgggtcatcc tgattcagac atagtgtttt
 181 gaatatatgg agtaagcaat gagttatact gtcggtacct atttagcggc gcttgtccag
 241 attggtctca agcatcactt cgcagtcgcg ggcgactaca acctcgtcct tcttgacaac
 301 ctgcttttga acaaaaacat ggagcaggtt tattgctgta acgaactgaa ctgcggtttc
 361 agtgcagaag gttatgctcg tgccaaagcg gacgcagcag ccgtcgttac ctacagcgtc
 421 ggtgcgcttt ccgcatttga tgctatcggt ggcgcctatg cagaaaacct tccggttatc
 481 ctgatctccg gtgctccgaa caacaatgat cacgctgctg gtcacgtgtt gcatcacgct
 541 cttggcaaaa ccgactatca ctatcagttg gaaatggcca agaacatcac ggccgcagct
 601 gaagcgattt acacccagaa agaagctccg gctaaaatcg atcacgtgat taaaactgct
 661 cttcgtgaga agaagccggt ttatctcgaa atcgcttgca acattgcttc catgccctgc
 721 gccgctcctg gaccggcaag cgcattgttc aatgacgaag ccagcgacga agcttctttg
 781 aatgcagcgg ttgaagaaac cctgaaattc atcgccaacc gcgacaaagt tgccgtcctc
 841 gtcggcagca agctgcgcgc agctggtgct gaagaagctg ctgtcaaatt tgctgatgct
 901 ctcggtggcg cagttgctac catggctgct gcaaaaagct tcttccagaa gaaaaccgca
 961 ttacatcggt acctcatggg tgaagtcagc tatccgggcg ttgaaaagac gatgaaagaa
1021 gccgatgcgg ttatcgctct ggctcctgtc ttcaacgact actccaccac tggttggacg
1081 gatattcctg atcctaagaa actggttctc gctgaaccgc gttctgtcgt cgttaacggc
1141 gttcgcttcc ccagcgttca tctgaaagac tatctgaccc gtttggctca gaaagtttcc
1201 aagaaaaccg gtgctttgga cttcttcaaa tccctcaatg caggtgaact gaagaaagcc
1261 gctccggctg atccgagtgc tccgttggtc aacgcagaaa tcgcccgtca ggtcgaagct
1321 cttctgaccc cgaacacgac ggttattgct gaaaccggtg actcttggtt caatgctcag
1381 cgcatgaagc tcccgaacgg tgctcgcgtt gaatatgaaa tgcagtgggg tcacatcggt
1441 tggtccgttc ctgccgcctt cggttatgcc gtcggtgctc cggaacgtcg caacatcctc
1501 atggttggtg atggttcctt ccagctgacg gctcaggaag tcgctcagat ggttcgcctg
1561 aaactgccgg ttatcatctt cttgatcaat aactatggtt acaccatcga agttatgatc
1621 catgatggtc cgtacaacaa catcaagaac tgggattatg ccggtctgat ggaagtgttc
1681 aacggtaacg gtggttatga cagcggcgct ggtaaaggcc tgaaggctaa aaccggtggc
1741 gaactggcag aagctatcaa ggttgctctg gcaaacaccg acggcccaac cctgatcgaa
1801 tgcttcatcg gtcgtgaaga ctgcactgaa gaattggtca aatggggtaa gcgcgttgct
1861 gcccgccaac agccgtaagc ctgttaacaa gctcctctag ttttt
```
//

Figure 10(C1)

```
<TITLE>GenBank Database Document Reader</TITLE>
<BODY BGCOLOR="#ffffe8"><PRE>
```

LOCUS    ZMOADHB    1747 bp  DNA       BCT    15-SEP-1989
DEFINITION  Z.mobilis alcohol dehydrogenase II (AdhB) gene, complete cds.
ACCESSION  M15394
NID       g155576
KEYWORDS   alcohol dehydrogenase II.
SOURCE     Z.mobilis (CP4) DNA, clone pLOI287.
  ORGANISM  Zymomonas mobilis
       Eubacteria; Proteobacteria; alpha subdivision; Zymomonas group;
       Zymomonas.
REFERENCE  1  (bases 1 to 1747)
  AUTHORS   Conway,T., Sewell,G.W., Osman,Y.A. and Ingram,L.O.
  TITLE     Cloning and sequencing of the alcohol dehydrogenase II gene from
        Zymomonas mobilis
  JOURNAL   J. Bacteriol. 169, 2591-2597 (1987)
  MEDLINE   87222181
COMMENT    Draft entry and computer-readable copy of sequence in [1] kindly
        provided by T.Conway (27-APR-1987).
        The Z.mobilis AdhII is an Fe-containing Adh peptide and shows 53.5%
        homology with the Adh4 of yeast (V.Williamson, UC Davis). There
        are tandem promoters located upstream of the transcription
        initiation sites.
FEATURES         Location/Qualifiers
    source       1..1747
              /organism="Zymomonas mobilis"
              /db_xref="taxon:542"
    mRNA         156..1634
              /note="adhB mRNA (alt.)"
    mRNA         256..1634
              /note="adhB mRNA (alt.)"
    CDS          432..1583
              /note="alcohol dehydrogenase II (EC 1.1.1.1)"
              /codon_start=1
              /db_xref="PID:g155577"
              /transl_table=11

/translation="MASSTFYIPFVNEMGEGSLEKAIKDLNGSGFKNALIVSDAFMNK

SGVVKQVADLLKAQGINSAVYDGVMPNPTVTAVLEGLKILKDNNSDFVISLGGGSPHD

CAKAIALVATNGGEVKDYEGIDKSKKPALPLMSINTTAGTASEMTRFCIITDEVRHVK

MAIVDRHVTPMVSVNDPLLMVGMPKGLTAATGMDALTHAFEAYSSTAATPITDACAL
K

Figure 10 (2)

AASMIAKNLKTACDNGKDMPAREAMAYAQFLAGMAFNNASLGYVHAMAHQLGGYYNLP

HGVCNAVLLPIIVLAYNASVVAGRLKDVGVAMGLDIANLGDKEGAEATIQAVRDLAASI

GIPANLTELGAKKEDVPLLADHALKDACALTNPRQGDQKEVEELFLSAF"
BASE COUNT    470 a    396 c    392 g    489 t
ORIGIN    DraI site.

```
   1 aaaggcaaaa tcggtaacca catctcaatt attaaacaat acttcataat aaaaagacaa
  61 ctttttcata atttgcataa gtcttgatgt aaaaaataca tatttagaaa gaacaagcag
 121 ccttgctcat caccgctgtc gcgagtagaa aaatctcggc tttcagaaaa agaggccgct
 181 tcgttaaaca gactataaat gtgctggaat aaagcgaacc ccttgatctg ataaaactga
 241 tagacatatt gcttttgcgc tgcccgattg ctgaaaatgc gtaaaaggtg attttactcg
 301 ttttcaggaa aaactttgag aaaacgtctc gaaaacggga ttaaaacgca aaaacaatag
 361 aaagcgattt cgcgaaaatg gttgttttcg ggttgttgct ttaaaactagt atgtagggtg
 421 aggttatagc tatggcttct tcaacttttt atattccttt cgtcaacgaa atgggcgaag
 481 gttcgcttga aaaagcaatc aaggatctta acggcagcgg ctttaaaaat gcgctgatcg
 541 tttctgatgc tttcatgaac aaatccggtg ttgtgaagca ggttgctgac ctgttgaaag
 601 cacagggtat taattctgct gtttatgatg gcgttatgcc gaacccgact gttaccgcag
 661 ttctggaagg ccttaagatc ctgaaggata acaattcaga cttcgtcatc tccctcggtg
 721 gtggttctcc ccatgactgc gccaaagcca tcgctctggt cgcaaccaat ggtggtgaag
 781 tcaaagacta cgaaggtatc gacaaatcta agaaacctgc cctgcctttg atgtcaatca
 841 acacgacggc tggtacggct tctgaaatga cgcgtttctg catcatcact gatgaagtcc
 901 gtcacgttaa gatggccatt gttgaccgtc acgttacccc gatggtttcc gtcaacgatc
 961 ctctgttgat ggttggtatg ccaaaaggcc tgaccgccgc caccggtatg gatgctctga
1021 cccacgcatt tgaagcttat tcttcaacgg cagctactcc gatcaccgat gcttgcgcct
1081 tgaaggctgc gtccatgatc gctaagaatc tgaagaccgc ttgcgacaac ggtaaggata
1141 tgccagctcg tgaagctatg gcttatgccc aattcctcgc tggtatggcc ttcaacaacg
1201 cttcgcttgg ttatgtccat gctatggctc accagttggg cggctactac aacctgccgc
1261 atggtgtctg caacgctgtt ctgcttccgc atgttctggc ttataacgcc tctgtcgttg
1321 ctggtcgtct gaaagacgtt ggtgttgcta tgggtctcga tatcgccaat ctcggtgata
1381 aagaaggcgc agaagccacc attcaggctg ttcgcgatct ggctgcttcc attggtattc
1441 cagcaaatct gaccgagctg ggtgctaaga agaagatgt gccgcttctt gctgaccacg
1501 ctctgaaaga tgcttgtgct ctgaccaacc cgcgtcaggg tgatcagaaa gaagttgaag
1561 aactcttcct gagcgctttc taatttcaaa acaggaaaac ggttttccgt cctgtcttga
1621 ttttcaagca aacaatgcct ccgatttcta atcggaggca tttgtttttg tttattgcaa
1681 aaacaaaaaa tattgttaca aattttaca ggctattaag cctaccgtca taaataattt
1741 gccattt
```
//
</PRE>

Figure 11 (1)

```
LOCUS       SYNINCALAC    7922 bp    DNA    circular SYN      13-MAY-1996
DEFINITION  Cloning vector pNO3097 (incA) gene, partial cds; (stbA and stbB)
            complete cds; beta-lactamase complete cds; lac repressor complete
            cds; ORF repA4; lambda repressor complete cds.
ACCESSION   L05669
NID         g208643
KEYWORDS    beta-lactamase; incA gene; lac repressor; lambda repressor.
SOURCE      Cloning vector pNO3097 DNA.
  ORGANISM  Cloning vector pNO3097
            Synthetic sequences; Cloning vehicles.
REFERENCE   1  (bases 1 to 7922)
  AUTHORS   Dunn,J.J. and Studier,F.W.
  TITLE     Nucleotide sequence from the genetic left end of bacteriophage T7
            DNA to the beginning of gene 4
  JOURNAL   J. Mol. Biol. 148 (4), 303-330 (1981)
  MEDLINE   82078034
REFERENCE   2  (bases 1 to 7922)
  AUTHORS   Ryder,T.B., Davidson,D.B., Rosen,J.I., Ohtsubo,E. and Ohtsubo,H.
  TITLE     Analysis of plasmid genome evolution based on nucleotide-sequence
            comparison of two related plasmids of Escherichia coli
  JOURNAL   Gene 17 (3), 299-310 (1982)
  MEDLINE   82262792
REFERENCE   3  (bases 1 to 7922)
  AUTHORS   Sanger,F., Coulson,A.R., Hong,G.F., Hill,D.F. and Petersen,G.B.
  TITLE     Nucleotide sequence of bacteriophage lambda DNA
  JOURNAL   J. Mol. Biol. 162 (4), 729-773 (1982)
  MEDLINE   83189071
REFERENCE   4  (bases 1 to 7922)
  AUTHORS   Masai,H., Kaziro,Y. and Arai,K.
  TITLE     Definition of oriR, the minimum DNA segment essential for
            initiation of R1 plasmid replication in vitro
  JOURNAL   Proc. Natl. Acad. Sci. U.S.A. 80 (22), 6814-6818 (1983)
  MEDLINE   84070720
REFERENCE   5  (bases 1 to 7922)
  AUTHORS   Larsen,J.E., Gerdes,K., Light,J. and Molin,S.
  TITLE     Low-copy-number plasmid-cloning vectors amplifiable by derepression
            of an inserted foreign promoter
  JOURNAL   Gene 28 (1), 45-54 (1984)
  MEDLINE   84237559
REFERENCE   6  (bases 1 to 7922)
  AUTHORS   Yanisch-Perron,C., Vieira,J. and Messing,J.
  TITLE     Improved M13 phage cloning vectors and host strains: nucleotide
            sequences of the M13mp18 and pUC19 vectors
  JOURNAL   Gene 33 (1), 103-119 (1985)
  MEDLINE   85180545
```

Figure 11 (2)

REFERENCE 7 (bases 1 to 7922)
  AUTHORS   Valentin-Hansen,P., Albrechtsen,B. and Love Larsen,J.E.
  TITLE     DNA-protein recognition: demonstration of three genetically
            separated operator elements that are required for repression of the
            Escherichia coli deoCABD promoters by the DeoR repressor
  JOURNAL   EMBO J. 5 (8), 2015-2021 (1986)
  MEDLINE   87004572
REFERENCE 8 (bases 1 to 7922)
  AUTHORS   Gerdes,K. and Molin,S.
  TITLE     Partitioning of plasmid R1. Structural and functional analysis of
            the parA locus
  JOURNAL   J. Mol. Biol. 190 (3), 269-279 (1986)
  MEDLINE   87060986
REFERENCE 9 (bases 1 to 7922)
  AUTHORS   Hu,M.C. and Davidson,N.
  TITLE     The inducible lac operator-repressor system is functional in
            mammalian cells
  JOURNAL   Cell 48 (4), 555-566 (1987)
  MEDLINE   87131068
REFERENCE 10 (bases 1 to 7922)
  AUTHORS   Tabuchi,A., Min,Y.N., Kim,C.K., Fan,Y.L., Womble,D.D. and
            Rownd,R.H.
  TITLE     Genetic organization and nucleotide sequence of the stability locus
            of IncFII plasmid NR1
  JOURNAL   J. Mol. Biol. 202 (3), 511-525 (1988)
  MEDLINE   89011976
REFERENCE 11 (bases 1 to 7922)
  AUTHORS   Womble,D.D. and Rownd,R.H.
  TITLE     Genetic and physical map of plasmid NR1: comparison with other
            IncFII antibiotic resistance plasmids
  JOURNAL   Microbiol. Rev. 52 (4), 433-451 (1988)
  MEDLINE   89181346
REFERENCE 12 (bases 1 to 7922)
  AUTHORS   Rose,R.E.
  TITLE     The nucleotide sequence of pACYC177
  JOURNAL   Nucleic Acids Res. 16 (1), 356 (1988)
  MEDLINE   88124215
REFERENCE 13 (bases 1 to 7922)
  AUTHORS   Masai,H. and Arai,K.
  TITLE     RepA protein- and oriR-dependent initiation of R1 plasmid
            replication: identification of a rho-dependent transcription
            terminator required for cis-action of repA protein
  JOURNAL   Nucleic Acids Res. 16 (14A), 6493-6514 (1988)
  MEDLINE   88289416
REFERENCE 14 (bases 1 to 7922)
  AUTHORS   Masai,H. and Arai,K.

Figure 11 (3)

TITLE    Leading strand synthesis of R1 plasmid replication in vitro is
primed by primase alone at a specific site downstream of oriR
JOURNAL   J. Biol. Chem. 264 (14), 8082-8090 (1989)
MEDLINE   89255240
REFERENCE   15 (bases 1 to 7922)
AUTHORS   Blomberg,P., Nordstrom,K. and Wagner,E.G.
TITLE    Replication control of plasmid R1: RepA synthesis is regulated by
CopA RNA through inhibition of leader peptide translation
JOURNAL   EMBO J. 11 (7), 2675-2683 (1992)
MEDLINE   92331620
REFERENCE   16 (bases 1 to 7922)
AUTHORS   Keener,J. and Nomura,M.
TITLE    Dominant lethal phenotype of a mutation in the -35 recognition
region of E. coli sigma 70
JOURNAL   Unpublished (1993)
FEATURES        Location/Qualifiers
     source      1..7922
                 /organism="Cloning vector pNO3097"
     misc_feature  1..1722
                 /note="NaeI-TaqI fragment from pJEL126 carrying the parA
                 partitioning locus of R1. This corresponds to positions
                 -28 to 1693 of ref. 4."
                 /citation=[7]
                 /citation=[10]
                 /citation=[8]
     misc_feature  1..7922
                 /note="plasmid copy number can be greatly amplified by
                 incubation at 42 degrees, which inactivates lambda
                 repressor and causes increased expression of the
                 replication protein; pNO3097 is a low copy cloning vector
                 with an R1 origin and partitioning system, amp resistance,
                 lac repressor and a polylinker downstream of the lac
                 promoter"
                 /citation=[16]
                 /citation=[5]
     gene         complement(106..168)
                 /gene="incA"
     CDS          complement(106..168)
                 /gene="incA"
                 /note="cis-acting incompatibility locus required for
                 stable maintenance of the plasmid"
                 /citation=[10]
                 /citation=[8]
                 /codon_start=1
                 /db_xref="PID:g940308"
                 /translation="MFWVLSGFVCQVYPISTINQ"

Figure 11 (4)

```
-35_signal    109..114
              /gene="incA"
-10_signal    131..136
              /gene="incA"
gene          211..1173
              /gene="stbA"
CDS           211..1173
              /gene="stbA"
              /note="StbA and StbB are both required for stable
              maintenance of the plasmid"
              /citation=[10]
              /citation=[8]
              /codon_start=1
              /db_xref="PID:g208644"
```

/translation="MLVFIDDGSTNIKLQWQESDGTIKQHISPNSFKREWAVPFGDKK

VFNYTLNGEQYSFDPTSPDAVVTTNIAWQYSDVNVVAVHHALLTSGLPVSEVDIVCTL

PLTEYYDRNNQPNTENIERKKANFRKKITLNGGDTFTIKDVKVMPESIPAGYEVLQEL

DELDSLLIIDLGGTTLDISQVMGKLSGISKIYGDSSLGVSLVTSAVKDALSLARTKGS

SYLADDIIIHRKDNNYLKQRINDENKISIVTEAMNEALRKLEQRVLNTLNEFSGYTHV
                MVIGGGAELICDAVKKHTQIRDERFFKTNNSQYDLVNGMYLIGN"

```
gene          1173..1631
              /gene="stbB"
CDS           1173..1631
              /gene="stbB"
              /note="one base was omitted in the sequence of ref.3
              resulting in a shorter reading frame, but was corrected in
              Genbank accessno. X04268 to agree with ref. 4"
              /citation=[10]
              /citation=[8]
              /codon_start=1
              /db_xref="PID:g208645"
```

/translation="MMDKRRTIAFKLNPDVNQTDKIVCDTLDSIPQGERSRLNRAALT

AGLALYRQDPRTPFLLCELLTKETTFSDIVNILRSLFPKEMADFNSSIVTQSSSQQEQ
              KSDEETKKNATKLIKLIQLLLSSLYPLSGWIKGTQSSYFLTSHYIIVIMK"

```
misc_feature  1723..2755
              /note="AatII-DraI fragment of pACYC 177 carrying the bla
              gene, positions 3567 to 659 of ref. 5, identical to pBR322
              sequence"
              /citation=[12]
```

Figure 11 (5)

CDS    1854..2714
       /note="25 micrograms/ml ampicillin does not inhibit
       growth, but 50 micrograms/ml causes some growth
       inhibition"
       /citation=[12]
       /codon_start=1
       /product="beta-lactamase"
       /db_xref="PID:g208646"

/translation="MSIQHFRVALIPFFAAFCLPVFAHPETLVKVKDAEDQLGARVGY

IELDLNSGKILESFRPEERFPMMSTFKVLLCGAVLSRVDAGQEQLGRRIHYSQNDLVE

YSPVTEKHLTDGMTVRELCSAAITMSDNTAANLLLTTIGGPKELTAFLHNMGDHVTRL

DRWEPELNEAIPNDERDTTMPAAMATTLRKLLTGELLTLASRQQLIDWMEADKVAGPL

LRSALPAGWFIADKSGAGERGSRGIIAALGPDGKPSRIVVIYTTGSQATMDERNRQIA
       EIGASLIKHW"
  misc_feature    2756..3903
       /note="lac DNA from position 48 of Genbank file ecolac (31
       bp upstream of start codon) to position 1179 (18bp
       downstream of stop codon); HindIII-SalI fragment of pRSV1
       carrying the gene for lac repressor flanked by linker DNA.
       EcoRI sites have been filled in"
       /citation=[9]
  CDS    2801..3883
       /note="start codon was changed from GTG to ATG, in this
       construction, the lacrepressor gene is cotranscribed with
       the gene for beta-lactamase"
       /citation=[9]
       /codon_start=1
       /product="lac repressor"
       /db_xref="PID:g208647"

/translation="MKPVTLYDVAEYAGVSYQTVSRVVNQASHVSAKTREKVEAAMAE

LNYIPNRVAQQLAGKQSLLIGVATSSLALHAPSQIVAAIKSRADQLGASVVVSMVERS

GVEACKAAVHNLLAQRVSGLIINYPLDDQDAIAVEAACTNVPALFLDVSDQTPINSII

FSHEDGTRLGVEHLVALGHQQIALLAGPLSSVSARLRLAGWHKYLTRNQIQPIAEREG

DWSAMSGFQQTMQMLNEGIVPTAMLVANDQMALGAMRAITESGLRVGADISVVGYD
DT

Figure 11 (c)

EDSSCYIPPSTTIKQDFRLLGQTSVDRLLQLSQGQAVKGNQLLPVSLVKRKTTLAPNT
QTASPRALADSLMQLARQVSRLESGQ"

misc_feature   3904..4100
           /note="DraI-BstBI fragment of pACYC177, from position 660
           to position 855 of ref. 5, included because of the method
           of construction, no known function"
           /citation=[12]
    misc_RNA     complement(4097)
           /note="5' end of RNA III inferred from known promoter
           within the R1 fragment"
           /citation=[2]
    misc_feature   4101..7454
           /note="NdeI-Eco47III fragment of pJEL126 carrying a fusion
           of the lambda Pr promoter to the replication genes of R1,
           controlled by heat sensitive lambda repressor"
           /citation=[7]
           /citation=[5]
    misc_feature   4101..6408
           /note="NdeI-BlgII fragmewnt of R1 extending from position
           2058 to position-258 of ref. 7, including the origin and
           genes for replication and copy number control"
           /citation=[2]
    CDS         complement(4159..4545)
           /note="ORF repA4"
           /citation=[2]
           /citation=[11]
           /codon_start=1
           /db_xref="PID:g208648"
           /translation="MHLPPQAAGPDRSHFSYNTQKQPPEKPRSSAEPKPQSPSLITEK RPRPGPKGRNRVAFNYECCNYIFIAVSLLAGSSQYTLVSGPHGPLTRRHAPTSGKPSS
GPLRPRTEALSWLKAGMVWQGWGWVR"

misc_feature   4181
           /note="site of initiation for leading strand DNA
           synthesis"
           /citation=[14]
    rep_origin     4548..4735
           /standard_name="oriR"
           /citation=[4]
           /direction=left
    misc_feature   complement(4736..4906)
           /standard_name="CIS"
           /note="the CIS sequence is required for cis-activation of
           oriR by the RepA protein"
           /citation=[13]

Figure 11 (7)

```
gene        complement(4908..5765)
            /gene="repA"
CDS         complement(4908..5765)
            /gene="repA"
            /note="RepA protein activates initiation of DNA
            replication at oriR, preferentially acting in cis.
            Synthesis of RepA is translationally coupled to that of
            tap"
            /citation=[15]
            /citation=[2]
            /codon_start=1
            /db_xref="PID:g208649"
            /transl_table=11

/translation="MTDLHQTYYRQVKNPNPVFTPREGAGTPKFREKPMEKAVGLTSR

FDFAIHVAHARSRGLRRRMPPVLRRRAIDALLQGLCFHYDPLANRVQCSITTLAIECG

LATESGAGKLSITRATRALTFLSELGLITYQTEYDPLIGCYIPTDITFTLALFAALDV

SEDAVAAARRSRVEWENKQRKKQGLDTLGMDELIAKAWRFVRERFRSYQTELQSRGIK

RARARRDANRERQDIVTLVKRQLTREISEGRFTANGEAVKREVERRVKERMILSRNRN
                YSRLATASP"
gene        complement(5762..5832)
            /gene="tap"
CDS         complement(5762..5832)
            /partial
            /gene="tap"
            /note="translation of tap is required for translation of
            repA protein"
            /citation=[15]
            /codon_start=1
            /db_xref="PID:g554559"
            /translation="MPGKVQDFFLCSLLLRIVSAGWC"
misc_RNA    5850..5940
            /standard_name="CopA"
            /note="CopA inhibits translation of tap, thus ultimately
            inhibiting expression of the RepA protein and initiation
            of plasmid replication"
            /citation=[15]
misc_RNA    complement(6016)
            /note="5' end of RNA II, which extends leftward, encodes
            tap and RepA proteins, and mostly terminates in the CIS
            region"
            /citation=[13]
```

Figure 11 (8)

```
            /citation=[2]
misc_feature    complement(6057..6321)
            /standard_name="CopB"
            /note="CopB regulates RNA II synthesis, in this plasmid it
            has been frameshifted by filling in the BglII site at
            6160, so copy number is expected to increase to about 5"
            /citation=[2]
            /citation=[5]
misc_feature    6409..7454
            /note="BglII-Eco47III fragment of lambda including the Pr
            promoter and the cI857 allele of lambda repressor
            extending from position 38,105 to 37,060 of ref. 13"
            /citation=[3]
-10_signal      complement(6498..6503)
protein_bind    6500..6516
            /citation=[3]
            /bound_moiety="lambda repressor"
misc_RNA        complement(6501)
            /note="5' end of the transcript from the powerful lambda
            Pr promoter, encodes RepA protein, regulated by
            heat-sensitive lambda repressor"
            /citation=[3]
            /citation=[5]
-35_signal      complement(6521..6526)
protein_bind    6524..6540
            /citation=[3]
            /bound_moiety="lambda repressor"
protein_bind    6547..6563
            /citation=[3]
            /bound_moiety="lambda repressor"
CDS             6574..7287
            /note="cI857 heat-sensitive allele of lambda repressor,
            shift to 42 causes inactivation of repressor, release of
            repression of the Pr promoter, and high expression of RepA
            protein"
            /citation=[3]
            /citation=[5]
            /codon_start=1
            /product="lambda repressor"
            /db_xref="PID:g208651"
```

/translation="MSTKKKPLTQEQLEDARRLKAIYEKKKNELGLSQESVADKMGMG

QSGVGALFNGINALNAYNAALLTKILKVSVEEFSPSIAREIYEMYEAVSMQPSLRSEY

EYPVFSHVQAGMFSPKLRTFTKGDAERWVSTTKKASDSAFWLEVEGNSMTAPTGSKPS

Figure 11(9)

FPDGMLILVDPEQAVEPGDFCIARLGGDEFTFKKLIRDSGQVFLQPLNPQYPMIPCNE
SCSVVGKVIASQWPEETFG"

misc_feature  7455..7727
  /note="SpeI-RsaI fragment from position 7697 to 7425 in
  ref. 15 of phage T7. Contains the early transcriptional
  terminator"
  /citation=[1]
stem_loop  complement(7572..7591)
  /note="early transcriptional terminator from phage T7,
  transcripts from the lac promoter and the polylinker
  region would terminate around position 7570"
  /citation=[1]
misc_feature  7728..7754
  /note="EcoRI-XbaI fragment of the pUC19 polylinker,
  positons 397 to 423 of ref. 16, KpnI is a unique site"
  /citation=[6]
misc_feature  7755..7790
  /note="custom polylinker provides unique sites for XbaI,
  XhoI, StuI, NdeI, PmlI, and EcoRI located downstream of
  the lac promoter"
misc_feature  7791..7914
  /note="EcoRI-AseI fragment from pUC18 contains the
  wild-type lac promoter and the lac operator, positons 1298
  to 1174 of the Genbank file ecolac, features listed below
  are from ecolac"
  /citation=[6]
protein_bind  7823..7840
  /note="transcription from the lac promoter is regulated by
  binding of lac repressor to the lac operator, addition of
  inducer (IPTG) prevents repressor binding"
  /bound_moiety="lac repressor"
misc_RNA  complement(7842)
  /note="5' end of lac mRNA, transcribed leftward into the
  polylinker"
-10_signal  complement(7849..7854)
-35_signal  complement(7873..7878)
protein_bind  7896..7911
  /note="the complex of cAMP and the CRP protein activates
  transcription of the lac promoter by binding to this site,
  growth in glucose gives low cAMP levels thus very low lac
  expression"
  /bound_moiety="cAMP receptor protein (CRP)"
misc_feature  7915..7922
  /note="XbaI-HincII fragment of the pUC19 polylinker,
  positions 424 to 431 of ref. 16"

Figure 11(o)

/citation=[6]
BASE COUNT    2161 a   1843 c   1908 g   2010 t
ORIGIN
     1 ggcggagtaa aaagaggagc ccggcgtcat cttttgttac ccgccaaaca aaacccaaaa
    61 acaacccata cccaacccaa taaaacacca aaacaagaca aataatcatt gattgatggt
   121 tgaaatgggg taaacttgac aaacaaaccc acttaaaacc caaaacatac ccaaacacac
   181 accaaaaaaa caccataagg agttttataa atgttggtat tcattgatga cggttcaaca
   241 aacatcaaac tacagtggca ggaaagcgac ggaacaatta acagcacat tagcccgaac
   301 agcttcaaac gcgagtgggc agtcccttt ggtgataaaa aggtctttaa ctacacactg
   361 aacggcgaac agtattcatt tgatccaacc agcccggatg ctgtagtcac aaccaatatc
   421 gcatggcaat acagcgacgt taatgtcgtt gcagtgcatc acgccttact gaccagtggt
   481 ctgccggtaa gcgaagtgga tattgtttgc acacttcctc tgacagagta ttacgacaga
   541 aataaccaac ccaatacgga aaatattgag cgtaagaaag caaacttccg gaaaaaaatt
   601 acattaaatg gcggggatac attcacaata aaagatgtaa aagtcatgcc tgaatctata
   661 ccggcaggtt atgaagttct acaagaactg gatgagttag attctttatt aattatagat
   721 ctcgggggca ccacattaga tatttctcag gtaatggga aattatcggg gatcagtaaa
   781 atatacggag actcatctct tggtgtctct ctggttacat ctgcagtaaa agatgccctt
   841 tctcttgcga gaacaaaagg aagtagctat cttgctgacg atataatcat tcacagaaaa
   901 gataataact atctgaagca acgaattaat gatgagaaca aaatatcaat agtcaccgaa
   961 gcaatgaatg aagcacttcg taaacttgag caacgtgtat taaatacgct caatgaattt
  1021 tctggttata ctcatgttat ggttataggc ggtggcgcag aattaatatg cgatgcagta
  1081 aaaaaacaca cacagattcg tgatgaacgt tttttcaaaa ccaataactc tcaatatgat
  1141 ttagttaacg gtatgtatct cataggtaat taatgatgga caagcgcaga accattgcct
  1201 tcaaactaaa tccagatgta aatcaaacag ataaaattgt ttgtgataca ctggacagta
  1261 tcccgcaagg ggaacgaagc cgccttaacc gggccgcact gacggcaggt ctggccttat
  1321 acagacaaga tccccggacc cctttccttt tatgtgagct gctgacgaaa gaaaccacat
  1381 tttcagatat cgtgaatata ttgagatcgc tatttccaaa agagatggcc gattttaatt
  1441 cttcaatagt cactcaatcc tcttcacaac aagagcaaaa aagtgatgaa gagaccaaaa
  1501 aaaatgcgac gaagctaata aaattaattc aattattatt gagttccctt tatccactat
  1561 caggctggat aaagggaact caatcaagtt attttcttac cagtcattac ataatcgtta
  1621 ttatgaaaata atcgtttgca ctgtctctgt tattcaggca atttcaataa aggcacttgc
  1681 tcacgctctg tcattttctg aaactcttca tgctgcattt cgcaggtggc acttttcggg
  1741 gaaatgtgcg cggaaccct atttgtttat ttttctaaat acattcaaat atgtatccgc
  1801 tcatgagaca ataaccctga taatgcttc aataatattg aaaaaggaag agtatgagta
  1861 ttcaacattt ccgtgtcgcc cttattcct tttttgcggc attttgcctt cctgtttttg
  1921 ctcacccaga aacgctggtg aaagtaaaag atgctgaaga tcagttgggt gcacgagtgg
  1981 gttacatcga actggatctc aacagcggta agatccttga gagttttcgc ccgaagaac
  2041 gttttccaat gatgagcact tttaaagttc tgctatgtgg cgcggtatta tcccgtgttg
  2101 acgccgggca agagcaactc ggtcgccgca tacactattc tcagaatgac ttggttgagt
  2161 actcaccagt cacagaaaag catcttacgg atggcatgac agtaagagaa ttatgcagtg
  2221 ctgccataac catgagtgat aacactgcgg ccaacttact tctgacaacg atcggaggac
  2281 cgaaggagct aaccgctttt ttgcacaaca tgggggatca tgtaactcgc cttgatcgtt
  2341 gggaaccgga gctgaatgaa gccataccaa acgacgagcg tgacaccacg atgcctgcag
  2401 caatggcaac aacgttgcgc aaactattaa ctggcgaact acttactcta gcttcccggc
  2461 aacaattaat agactggatg gaggcggata agttgcagg accacttctg cgctcggccc
  2521 ttccggctgg ctggtttatt gctgataaat ctggagccgg tgagcgtggg tctcgcggta

Figure 11 (11)

```
2581 tcattgcagc actggggcca gatggtaagc cctcccgtat cgtagttatc tacacgacgg
2641 ggagtcaggc aactatggat gaacgaaata gacagatcgc tgagataggt gcctcactga
2701 ttaagcattg gtaactgtca gaccaagttt actcatatat actttagatt gatttagctt
2761 gaattaattc ccggaagaga gtcaattcag ggtggtgaat atgaaaccag taacgttata
2821 cgatgtcgca gagtatgccg gtgtctctta tcagaccgtt tcccgcgtgg tgaaccaggc
2881 cagccacgtt tctgcgaaaa cgcgggaaaa agtggaagcg gcgatggcgg agctgaatta
2941 cattcccaac cgcgtggcac aacaactggc gggcaaacag tcgttgctga ttggcgttgc
3001 cacctccagt ctggccctgc acgcgccgtc gcaaattgtc gcggcgatta aatctcgcgc
3061 cgatcaactg ggtgccagcg tggtggtgtc gatggtagaa cgaagcggcg tcgaagcctg
3121 taaagcggcg gtgcacaatc ttctcgcgca acgcgtcagt gggctgatca ttaactatcc
3181 gctggatgac caggatgcca ttgctgtgga agctgcctgc actaatgttc cggcgttatt
3241 tcttgatgtc tctgaccaga cacccatcaa cagtattatt ttctcccatg aagacggtac
3301 gcgactgggc gtggagcatc tggtcgcatt gggtcaccag caaatcgcgc tgttagcggg
3361 cccattaagt tctgtctcgg cgcgtctgcg tctggctggc tggcataaat atctcactcg
3421 caatcaaatt cagccgatag cggaacggga aggcgactgg agtgccatgt ccggttttca
3481 acaaaccatg caaatgctga atgagggcat cgttcccact gcgatgctgg ttgccaacga
3541 tcagatggcg ctgggcgcaa tgcgcgccat taccgagtcc gggctgcgcg ttggtgcgga
3601 tatctcggta gtgggatacg acgataccga agacagctca tgttatatcc cgccgtcaac
3661 caccatcaaa caggattttc gcctgctggg gcaaaccagc gtggaccgct tgctgcaact
3721 ctctcagggc caggcggtga agggcaatca gctgttgccc gtctcactgg tgaaaagaaa
3781 aaccaccctg gcgcccaata cgcaaaccgc ctctccccgc gcgttggccg attcattaat
3841 gcagctggca cgacaggttt cccgactgga aagcgggcag tgagcgcaac gcaattaatg
3901 tcgaaaaact tcattttaaa tttaaaagga tctaggtgaa gatccttttt gataatctca
3961 tgaccaaaat cccttaacgt gagttttcgt tccactgagc gtcagacccc gtaataagat
4021 gatcttcttg agatcgtttt ggtctgcgcg taatctcttg ctctgaaaac gaaaaaaccg
4081 ccttgcaggg cggtttttcg tatgatacag gagtaaaacc gccgaagccc ggcgtaagcc
4141 ggtactgatt gatagatttc accttaccca tccccagccc tgccagacca tacccgcttt
4201 cagccatgag agagcttctg tgcgcggtcg gagtggtccc gacgagggtt tacccgaagt
4261 cggggcgtgt ctccgcgtta gcgggccgtg agggccgctt acgagcgtgt actgagaact
4321 tccagcgaga agactgacag cgatgaagat gtagttacaa cattcataat taaaagcgac
4381 tctgttccgg ccctttgggc cggggcgggg ccgcttttca gttatgaggg aggggctttg
4441 tggtttcggt tctgcgctgg accggggttt ttctggaggt tgtttttgtg tgttgtaact
4501 aaagtggctc cggtcggggc ccgccgcttg cggtgggagg tgcatatctg tctgtccaca
4561 ggacaggcag tgaataggtt ttcttttaa atgaatgtaa ttaagtagtt taaaggagat
4621 ataaacaggt gtttaaaaga tacattgcac cctgtaagac tggcggctgg cgctttatga
4681 catgaacggt tgtaaccttta tggggaagtc ccttgcagtt aaatgtggat aagcaaaatt
4741 ccccgtcgct gaggcgtatt ttgtattaaa aacaggggga atcggatgct ccagaaggtg
4801 gatgatgaga ttgttttttg catgcgacgc tgtttttttg tgcaccggcg ggcttcaggc
4861 gtgcggatgc ctccggcgca ggccggatta ttctgaggag atcactttca gggagaagct
4921 gtggccagcc ggctgtaatt gcggttacgt gacagaatca tgcgctcctt cacacgacgc
4981 tccacttcgc gttttaccgc ctcaccatta gcagtgaagc gtccttccga gatttcacgc
5041 gtcagctgcc gtttcactag ggtgacgata tcctgacgtt ctctgttcgc atcacgacgc
5101 gcacgggcac gttttattcc acgggactga agctctgtct ggtaactgcg gaaacgctca
5161 cgcacaaaac gccaggcttt cgctatcagc tcatccatac ccagggtatc cagcccctgc
5221 ttttgcgct gtttgttttc ccattcaaca cgactgcggc gcgcagctgc cactgcatcc
5281 tcagacacat caagggcagc aaacagagcc agtgtgaacg tgatgtcggt cggaatgtag
```

Figure 11(12)

```
5341 cacccgataa gcgggtcata ttccgtctgg taggtaatca gtcccagctc tgacaggaac
5401 gtcagggccc gggtggcacg ggtgatggag agttttcctg caccggactc tgtcgccagt
5461 ccgcactcaa tggccagtgt ggtgatggaa cactggacgc ggttggccag cgggtcatag
5521 tggaaacaca gcccctgcag cagcgcatca atagcccgtc gacgcagcac cggtggcatg
5581 cgccgacgca gaccacggga acgggcatgc gccacatgaa tggcgaaatc aaaacgggag
5641 gtgaggccca ccgccttttc catcggtttt tcgcggaact tcggcgttcc ggcaccttca
5701 cggggagtga acaccggatt cgggttcttt acctggcggt aatacgtttg gtgaagatca
5761 gtcacaccat cctgcactta caatgcgcag aaggagcgag cacagaaaga agtcttgaac
5821 ttttccgggc atataactat actccccgca tagctgaatt gttggctata cggtttaagt
5881 gggccccggt aatcttttcg tactcgccaa agttgaagaa gattatcggg gttttgctt
5941 ttctggctcc tgtaaatcca catcagaacc agttccttgc caccttacgg cgtggcagcc
6001 acaaaattcc ttaaacgatc agtaatctag ctagctacgc cacaaagtaa agtctttac
6061 tttagtatat ccagtctctg cagttcatct ttgatgattt tctcaacgaa ctgagcctgt
6121 gttatcccct ctctctcgca gtactcaacc atgagatcga tctttcagag gatttttgac
6181 aaaaactttt atctctttgt gtgtaagacg ttttcttgca acagcggcca tttgtttctc
6241 agagtcagtc ataggcttac ctctgcgcac aaaccgcttt tgactcaatg aggaagtcac
6301 tgcattttct gtctgcgaca tctcgcctcc tcaatactca aacagggatc gtttcgcaga
6361 ggatactaca gttttttgaa atcagcaact tgagaattgt gacgaagatc tttagctgtc
6421 ttggtttgcc caaagcgcat tgcataatct ttcagggtta tgcgttgttc catacaacct
6481 ccttagtaca tgcaaccatt atcaccgcca gaggtaaaat agtcaacacg cacggtgtta
6541 gatatttatc ccttgcggtg atagatttaa cgtatgagca caaaaaagaa accattaaca
6601 caagagcagc ttgaggacgc acgtcgcctt aaagcaattt atgaaaaaaa gaaaaatgaa
6661 cttggcttat cccaggaatc tgtcgcagac aagatgggga tggggcagtc aggcgttggt
6721 gctttattta atggcatcaa tgcattaaat gcttataacg ccgcattgct tacaaaaatt
6781 ctcaaagtta gcgttgaaga atttagccct tcaatcgcca gagaaatcta cgagatgtat
6841 gaagcggtta gtatgcagcc gtcacttaga agtgagtatg agtaccctgt tttttctcat
6901 gttcaggcag ggatgttctc acctaagctt agaacccttta ccaaaggtga tgcggagaga
6961 tgggtaagca caaccaaaaa agccagtgat tctgcattct ggcttgaggt tgaaggtaat
7021 tccatgaccg caccaacagg ctccaagcca agctttcctg acggaatgtt aattctcgtt
7081 gaccctgagc aggctgttga gccaggtgat ttctgcatag ccagacttgg gggtgatgag
7141 tttaccttca agaaactgat cagggatagc ggtcaggtgt ttttacaacc actaaaccca
7201 cagtacccaa tgatcccatg caatgagagt tgttccgttg tggggaaagt tatcgctagt
7261 cagtggcctg aagagacgtt tggctgatcg gcaaggtgtt ctggtcggcg catagctgat
7321 aacaattgag caagaatctt catcgaatta ggggaatttt cactcccctc agaacataac
7381 atagtaaatg gattgaatta tgaagaatgg tttttatgcg acttaccgca gcaaaaataa
7441 agggaaagat aagcctagtg ctacttgagg gtataccgca agaatatacg caagcgtcag
7501 gatagctgcc aaagccgcaa ggaatttacc aaccttctta aacataaagt gtctccttat
7561 aaacgcagaa aggcccaccc gaaggtgagc cagtgtgatt acatttctc ttgagggttg
7621 tcctcggtgc cacggaacat tacgaacgat gggtgccgca aagagccatc aggtgtttcc
7681 tccatgtagc taatttgaca cgcccagcca tcgtaagggt taatagtaat tcgagctcgg
7741 taccccgggga tcctctagag ctcgaggcct catatggatc cacgtgaatt cgtaatcatg
7801 tcatagctgt ttcctgtgtg aaattgttat ccgctcacaa ttccacacaa catacgagcc
7861 ggaagcataa agtgtaaagc ctggggtgcc taatgagtga gctaactcac attactagag
7921 tc
```

GENETICALLY MODIFIED CYANOBACTERIA FOR THE PRODUCTION OF ETHANOL, THE CONSTRUCTS AND METHOD THEREOF

This application is a divisional of and claims priority to patent application Ser. No. 09/026,845 filed Feb. 20, 1998 in the United States Patent and Trademark Office, now U.S. Pat. No. 6,306,639 issued Oct. 23, 2001, which is a continuation-in-part application of and claims priority to prior application Ser. No. 08/801,331 filed on Feb. 19, 1997 now abandoned.

FIELD OF INVENTION

This invention relates to the genetic modification of Cyanobacteria for the production of ethanol. In particular, this invention relates to the genetic modification of Synechococcus by incorporating the genetic information encoding for pyruvate decarboxylase (pdc) and alcohol dehydrogenase (adh).

BACKGROUND

Ethanol is an energy source which is particularly attractive because it can be utilized with little waste. In addition, ethanol derived from living organisms is an attractive alternative to petroleum based fuels because it is a renewable resource.

A number of alternatives for the production of ethanol from living organisms have been investigated using microorganisms.

The production of ethanol by microorganisms has, in large part, been investigated using the yeast Saccharomyces and bacteria Zymomonas, which is a facultative anaerobic. Both of these microorganisms contain the genetic information to produce enzymes pdc and adh, which enzymes are used to produce ethanol from pyruvate, a product of the glycolytic pathway.

U.S. Pat. No. 4,242,455 to Muller et al. describes a continuous process in which an aqueous slurry of carbohydrate polymer particles, such as starch granules and/or cellulose chips, fibres, etc., are acidified with a strong inorganic acid to form a fermentable sugar. The fermentable sugar is then fermented to ethanol with at least two strains of Saccharomyces. U.S. Pat. No. 4,350,765 to Chibata et al. describes a method of producing ethanol in a high concentration by using an immobilized Saccharomyces or Zymomonas and a nutrient culture broth containing a fermentative sugar. U.S. Pat. No. 4,413,058 to Arcuri et al. describes a new strain of Zymomonas mobilis which is used to produce ethanol by placing the microorganism in a continuous reactor column and passing a stream of aqueous sugar through said column.

PCT Application WO/88/09379 to Hartley et al. describes the use of facultative anaerobic thermophilic bacteria strains which produce ethanol by fermenting a wide range of sugars, including cellobiose and pentoses. These bacteria strains contain a mutation in lactate dehydrogenase. As a result, these strains which would normally produce lactate under anaerobic conditions, produce ethanol instead.

In addition, Escherichia coli has been genetically altered to produce ethanol by inserting the genetic material encoding for the adh and pdc enzymes using the pLOI295 plasmid. The genetic material encoding the pdc enzyme was isolated from Zymomonas mobilis. This altered Escherichia coli produces ethanol; however, it still requires a variety of organic substrates for bacterial metabolism and growth. (Ingram, et al. (1987), "Genetic Engineering of Ethanol Production in Escherichia coli" (Appl. Environ Microbiol. 53: 2420–2425)

All of the above prior art describe microorganisms which utilize a carbohydrate/sugar substrate to produce ethanol. As such, these processes are costly because a feed substrate of carbohydrates/sugars is required in order for the microorganisms to be able to produce ethanol. Hence, the cost of these systems is a deterrent to the refinement and scale up of such systems for the production of ethanol.

It is highly desirable to find a microorganism which can effectively produce ethanol wherein said microorganism requires minimal feed substrate.

SUMMARY OF THE PRESENT INVENTION

In an aspect of the present invention, there is provided genetically modified photosynthetic Cyanobacteria which are capable of producing ethanol. The Cyanobacteria are genetically modified by the insertion of DNA fragments encoding the enzymes pdc and adh. Consequently, the enzymes pdc and adh are produced in vivo by the genetically modified Cyanobacteria; which enzymes convert pyruvate to acetaldehyde and acetaldehyde to ethanol, respectively. In particular, Synechococcus is a preferred Cyanobacteria of the present invention. In a preferred embodiment, transformed Synechococcus produce ethanol in recoverable quantities of at least 1.7 $\mu$mol of ethanol per mg of chlorophyll per hour.

In a further aspect of the present invention, there is provided genetically modified Cyanobacteria which contain constructs comprising a temperature inducible gene so that the ethanol is produced only once a particular temperature is reached. In a particular embodiment, the construct comprises the CI857 temperature inducible gene. The CI857 temperature inducible gene maybe used in the form of the CI-PL promoter, EMBL Accessive No. L05669, SEQ. ID. No.7.

In a further aspect of the present invention, there is provided genetically modified Cyanobacteria which contain constructs comprising DNA fragments encoding the pdc and adh enzymes obtained from the Zymomonas mobilis plasmid pLOI295.

In a further aspect of the present invention, the Cyanobacteria is Synechococcus PCC 7942 or other transformable strains capable of producing ethanol when a construct comprising DNA fragments encoding pdc and adh enzymes from the pLOI295 plasmid is transformed into the Synechococcus.

In a further aspect of the present invention, there is provided genetically modified Cyanobacteria containing constructs comprising DNA fragments from the Zymomonas mobilis plasmid pLOI295 encoding the pdc and adh enzymes wherein the DNA fragment encoding the pdc enzyme is listed in the European Molecular Biology Laboratories ("EMBL") as Accession No. M15393 and as described in Conway et al. (1987) J. Bacterial 169: 949–954 SEQ. ID. No. 5, or a gene sequence that encodes the pdc enzyme and is capable of expression in Cyanobacteria.

In a further aspect of the present invention, there is provided genetically modified Cyanobacteria containing constructs comprising DNA fragments from the Zymomonas mobilis plasmid pLOI295 encoding the pdc and adh enzymes wherein the DNA fragment encoding the adh enzyme is adh II listed in the EMBL as Accession No. M15394 and as described in Conway et al. (1987) J. Bacterial 169: 2591–2597, SEQ. ID. No. 6 or a gene sequence that encodes the adh enzyme and that is capable of expression in Cyanobacteria.

In another aspect of the present invention there is provided a genetically modified Cyanobacteria capable of producing ethanol produced according to the following steps:

a. selecting an appropriate promoter;

b. ligating said promotor to pdc and adh encoding DNA sequence;

c. cloning said ligated promoter and said pdc and adh encoding DNA into an appropriate construct;

d. transforming the construct into the Cyanobacteria

In a preferred embodiment the modified Cyanobacteria is a modified Synechococcus PCC 7942. Constructs produced according to these steps include constructs selected from the group consisting of pCB4-Rpa, pCB4-LRpa and pCB4-LR(TF)pa.

In a further aspect of the present invention, there is provided a construct comprising a promoter from Synechococcus operatively linked to genes encoding pdc and adh enzymes from the Zymomonas mobilis pLOI295 plasmid.

In a further aspect of the present invention there is provided a construct wherein the promoter comprises an rbcLS operon of Synechococcus. In another aspect the promoter further comprises a lacZ operon of Escherichia coli.

In a further aspect of the present invention there is provided a construct wherein the DNA fragments encoding the pdc and adh enzymes are listed in EMBL as Accession No. M15393 and M15394, SEQ. ID. Nos. 5 and 6, respectively, or analogous sequences thereof that include encoding for the pdc enzyme and the adh enzyme, respectively.

In a further aspect of the present invention, there is provided constructs encoding the pdc and adh enzymes wherein the constructs include a temperature inducible gene CI857.

In a further aspect of the invention, there is provided a promoter capable of being used in a construct encoding pdc and adh enzymes obtained from Zymomonas mobilis, wherein the promoter comprises a rbcLS operon of Synechococcus.

In a further aspect of the present invention, there is provided a promoter capable of being used in a construct encoding the pdc and adh enzymes obtained from Zymomonas mobilis, wherein the promoter comprises a rbcLS operon of Synechococcus and a lacZ operon of Escherichia coli.

In a further aspect of the present invention there is provided a CI-PL promoter which is temperature inducible and is capable of being used in a construct encoding pdc and adh enzymes obtained from Zymomonas mobilis wherein said promoter is activated only once a particular temperature is reached.

In a further aspect of the present invention there is provided a process for making genetically modified Cyanobacteria by incorporating a construct encoding the pdc and adh enzymes from the Zymomonas mobilis pLOI295 plasmid, or other suitable source of pdc and adh enzymes, according to the following steps:

a. harvesting cells of the Cyanobacteria;

b. adding the construct to the harvested Cyanobacteria cells;

c. incubating the construct and the Cyanobacteria cells such that the construct is transformed into the Cyanobacteria cells;

d. plating the incubated constructs and Cyanobacteria cells on plates containing ampicillin and incubating under appropriate growth conditions;

e. selecting the transformed ampicillin resistant Cyanobacteria cells.

In a further aspect of the present invention, there is provided a process for producing ethanol using genetically modified Cyanobacteria which comprises the steps of: culturing in a culture medium Cyanobacteria, wherein the Cyanobacteria contains a construct comprising DNA fragments encoding pdc and adh enzymes obtained from the Zymomonas mobiles pLOI295 and accumulating ethanol in the culture medium. In a preferred embodiment, the process for producing ethanol includes a construct which comprises a temperature inducible gene and the process comprises the further step of increasing the temperature of the culture medium to induce expression of the pdc and adh genes.

DETAILED DESCRIPTION OF THE DRAWINGS

The invention will now be better understood with reference to the following figures and examples, and corresponding description, which are illustrative of preferred embodiments of the invention. The invention should not be limited by the drawings.

Figure 6:
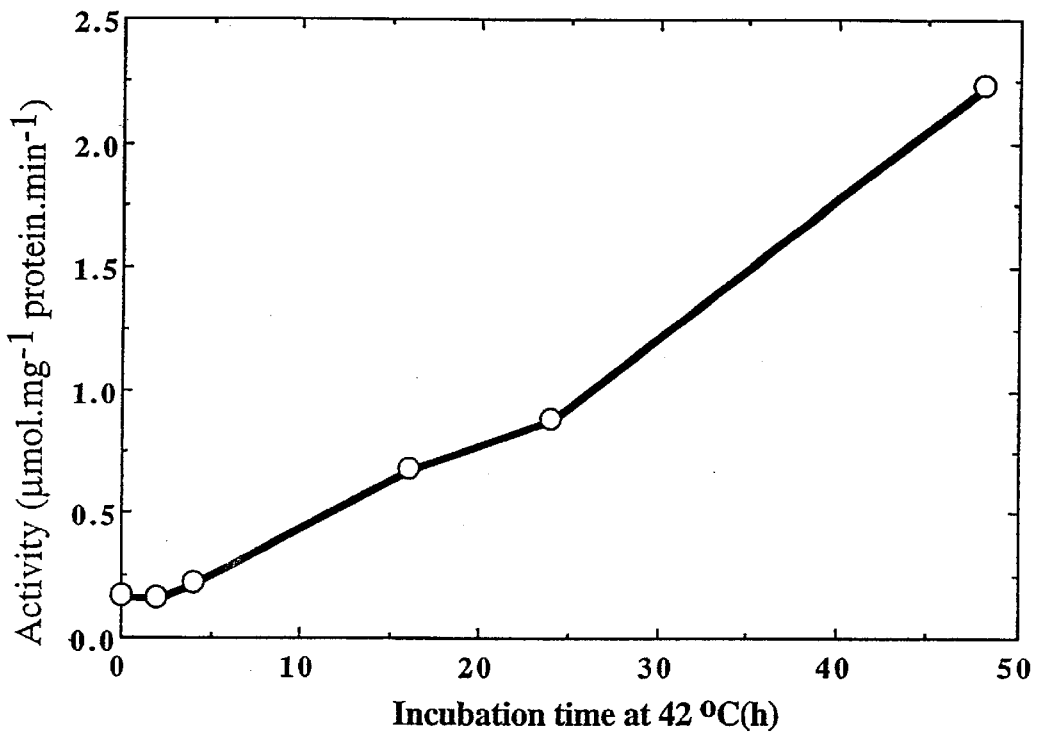

FIG. 6 is an illustration of a graph on the incubation time of Synechococcus PCC 7942 cells transformed with the vector pCB4pa. at 42 degrees Celsius versus the activity of pyruvate decarboxylase. The cells were first grown at 30 degree Celsius and then transferred to 42 degrees Celsius. Cells were harvested at intervals to determine the activity of pyruvate decarboxylase.

Figure 7:
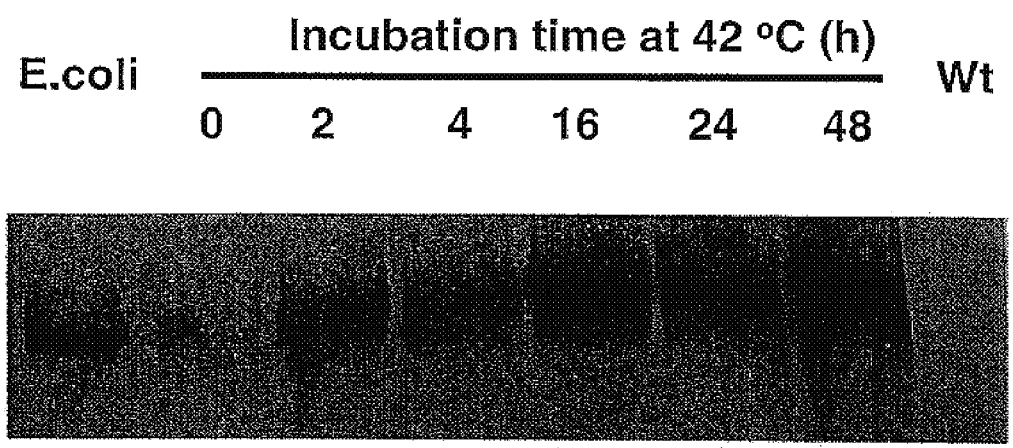

FIG. 7 is an illustration of the induction of adh expression at 42 degrees Celsius for Synechococcus PCC 7942 as compared to E. coli and wild type Synechococcus.

Figure 8:
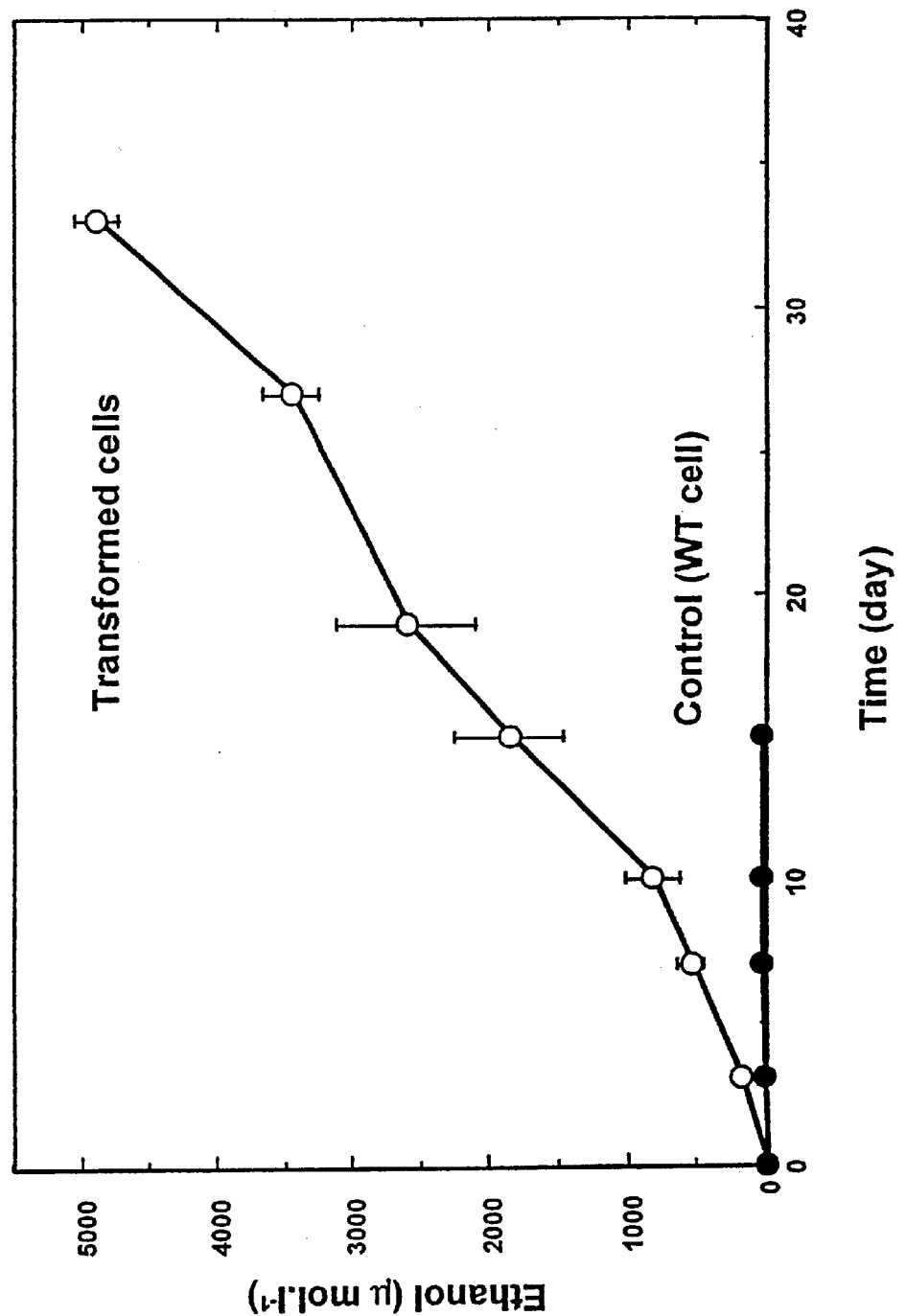

FIG. 8 is an illustration of the induction time of Synechococcus PCC 7942 versus ethanol production in of Synechococcus PCC 7942 in cells transformed with pCB4-Rpa. Synechococcus PCC 7942 Wt cells and the cells transformed with the shuttle vector pCB4-Rpa were grown in a liquid batch culture. The culture was sampled at intervals to assay the amount of ethanol. The bars indicate the S.D. for 4–6 different samples.

FIG. 9 is a description of the pdc gene identified as SEQ ID. No.5.

FIG. 10 is a description of the adh gene identified as SEQ. ID. No. 6.

FIG. 11 is a description of the CI-PL promoter identified as SEQ. ID. No. 7.

All like letter designations refer to the same sites on the different maps of the plasmid constructs in the figures as follows: AMP$^R$ (ampicillin resistant); PDC (pyruvate decarboxylase); ADH (alcohol dehydrogenase); ATG (start codon); L (lacZ promoter); R (rbcLS promoter); R' (EcoRI);

B (BamHI); S (SalI); X (XbaI); X/P (XbaI/PvuII fusion); Xh/B (XhoI/BamHI fusion); T (transcription terminator) and CI-PL (temperature inducible gene and bacterial phage left-ward promoter).

DETAILED DESCRIPTION

Cyanobacteria are photosynthetic bacteria which require light, inorganic elements, water and a carbon source, generally $CO_2$, to metabolise and grow.

Cyanobacteria are photosynthetic procaryotes which carry out oxygenic photosynthesis. The main product of the metabolic pathway of Cyanobacteria during aerobic conditions is oxygen and carbohydrate reserves.

The initial product of photosynthetic fixation of $CO_2$ is 3-phosphoglycerate. 3-phosphoglycerate is used in the Calvin Cycle to regenerate ribulose-1,5-biphosphate, which is the acceptor of $CO_2$. There are two major branching points where the intermediates of the Calvin Cycle are connected to other metabolic pathways. At one point, fructose-6-phosphate is converted into glucose-6-phosphate and glucose-phosphate, which are the substrates for the pentose phosphate pathway, the synthesis of cellulose (a major component of the cell wall) and the synthesis of glycogen (the major form of carbohydrate reserve). At the other branching point, 3-phosphoglycerate is converted into 2-phosphoglycerate, phosphoenolpyruvate and pyruvate in a sequence of reactions catalysed by phosphoglycerate mutase, enolase and pyruvate kinase, respectively. Pyruvate is directed to the partial TCA cycle for the synthesis of amino acids, nucleotides, etc. in aerobic conditions. Pyruvate is also the substrate for ethanol synthesis.

To convert the carbohydrate reserves into ethanol, the carbohydrate reserves must be diverted to the glycolytic pathway. The presumed pathway for carbohydrate reserve metabolism in Cyanobacteria is through both the glycolytic pathway and the phosphogluconate pathway. For the purposes of ethanol formation, the glycolytic pathway is of primary importance. Although not well characterized in Cyanobacteria, glycogen is presumed to be metabolized into glucose 1—phosphate by a combination of glycogen phosphorylase and a 1,6-glycosidase. Phosphoglucomutase, phosphoglucoisomerase and phosphofructokinase convert glucose 1-phosphate into a molecule of fructose1,6-bisphosphate. This compound is cleaved by the action of aldolase and triose phosphate isomerase into two molecules of glyceraldehyde 3-phosphate. This compound is converted into pyruvate through sequential series of reactions catalysed by glyceraldehyde 3-phosphate dehydrogenase, phosphoglycerate kinase, phosphoglycerate mutase, enolase and pyruvate kinase, respectively.

In some algae and Cyanobacteria strains, a small amount of ethanol is synthesized as a fermentation product under dark and anaerobic conditions (Van der Oost et al., 1989; Heyer and Krumbein, 1991). However, the dark-anaerobic fermentation process is generally operating at a very low level, only sufficient for the survival of the organisms under such stress conditions. The synthesis of ethanol under dark and anaerobic conditions is dependent on the degradation of glycogen reserve, as described above. Moreover, it has been found that ethanol synthesis under anaerobic conditions is totally inhibited by light. Thus, in photosynthetic microorganisms ethanol synthesis is not coupled with photosynthesis and can actually be inhibited by photosynthesis.

Therefore, it has been observed that Cyanobacteria do not utilize $CO_2$ to produce ethanol. Furthermore, there are no known photosynthetic microorganisms, including genetically engineered photosynthetic microorganisms, which produce ethanol in relatively substantial amounts. A further complication is that some photosynthetic organisms have been shown to be inhibited by ethanol such that the addition of ethanol to the culture medium inhibits the expression of genes involved in photosynthesis.

In the present invention, it has been found that Cyanobacteria can be successfully genetically engineered to utilize a direct flux of carbon from $CO_2$ to 3-phosphoglycerate, and to pyruvate, to produce a quantifiable amount of ethanol as opposed to utilizing a glycogen reserve as is done under anaerobic and dark conditions.

It has been found that Cyanobacteria can be genetically modified by introducing genes encoding for the enzymes pdc and adh to produce ethanol. In particular, a pathway for ethanol synthesis has been created in Synechococcus PCC 7942, and this pathway is directly coupled with photosynthesis.

By incorporating the genetic material encoding the pdc and adh enzymes into the Synechococcus genetic material, a Synechococcus capable of producing ethanol is created. It was surprisingly found that pdc and adh enzymes from an obligate anaerobe, Z. mobilis, could be successfully inserted, expressed and be fully functional in Synechoccocus. Although pdc and adh enzymes from Z. mobilis had been transformed into E. coli. As described in Ingram, et al. (1987), "Genetic Engineering of Ethanol Production in Escherichia coli" (Appl. Environ Microbiol. 53: 2420–2425), E. coli is a facultative anaerobic, it has an inducible adh gene and it is grown in a carbohydrate medium and said carbohydrates are used to produce ethanol. On the other hand, Cyanobacteria are photosynthetic organisms and are recalcitrant to taking up organic substances for any purpose, including growth or ethanol production. Hence, E. coli is a very different system than Cyanobacteria. E. coli is more like Z. mobilis which depends on feed stock for growth and ethanol production. There are other sources of pdc and adh enzymes, including Saccharomyces cerevisciae.

It has also been found that ethanol synthesis may compete with cell growth for the use of carbon. Therefore, it would be beneficial to have an inducible system for ethanol synthesis so that cell growth and ethanol synthesis could be carried out in two phases. During the first phase, Cyanobacteria cells are cultured under non-induced conditions, so that the cell culture can reach a high density and accumulate a large amount of carbohydrates. Ethanol synthesis is then induced in the second phase.

In particular it was discovered that a temperature inducible system could be successfully developed to induce the production of ethanol in Cyanobacteria. A pdc-adh operon with the bacterial phage left-ward promoter ($P_L$) and a temperature sensitive repressor gene CI857 were employed to produce a temperature inducible system for producing ethanol in Cyanobacteria.

It is believed that at a non-permissible temperature (low temperature, 30 degrees Celsius), the repressor binds to the operator sequence, and thus prevents RNA polymerase from initiating transcription at the $P_L$ promoter. Therefore, the expression of pdc-adh genes is repressed. When the cell culture is transferred to a permissible temperature (37–42 degrees Celsius), the repressor can not bind to the operator. Therefore, RNA polymerase can initiate the transcription of the pdc-adh gene.

The Examples below exemplify the four different constructs: pCB4-Rpa, pCB4-LRpa, pCB4-LR(TF)pa and pCB4-CPpa: the synthesis of these constructs; the incorporation of these constructs into Synechococcus PCC 7942 and the production of ethanol from said genetically modified Synechococcus. Other transformable strains of Synechococcus which are capable of producing ethanol when a construct containing DNA encoding the adh and pdc enzyme is transformed into the Synechococcus may also be used.

Figure 1:
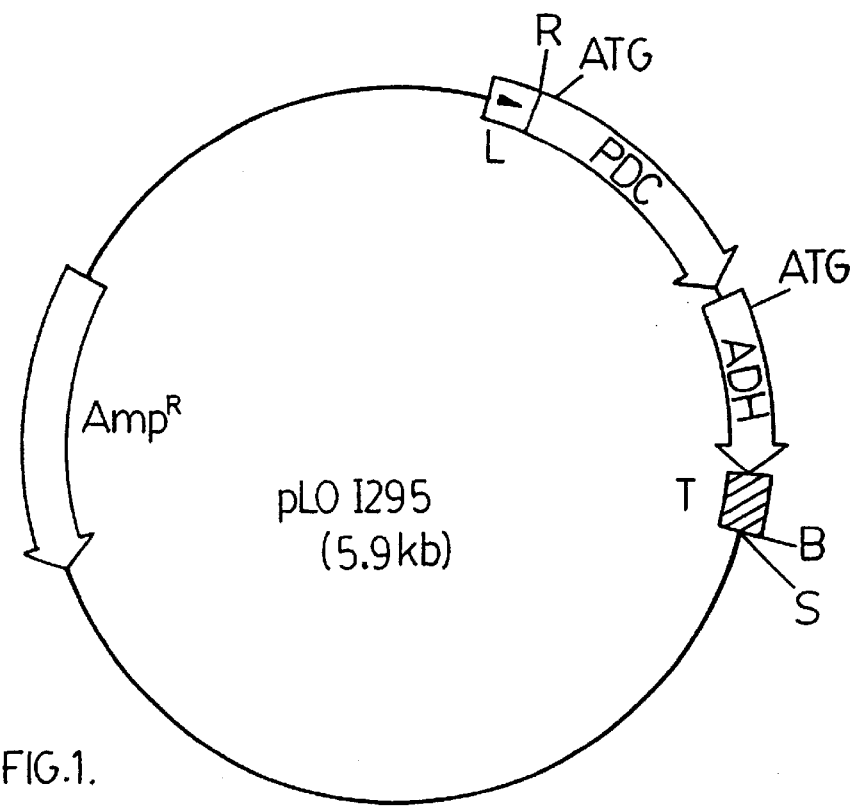
FIG. 1 is an illustration of the map of the plasmid pLOI295 containing the DNA fragments encoding for pdc and adh.

In the examples below, Synechococcus PCC 7942, which is available from the Pasteur Culture Collection, Rue de Dr. Roux, Paris, France, was used. The genes encoding the pdc and adh enzymes of *Zymomonas mobilis* were excised from the pLOI295 plasmid, which is available from Dr. L. 0. Ingram, Dept. of Microbiology and Cell Science, University of Florida, Gainsville, Fla., U.S.A. 32611. (See also: Ingram et al., (1987) "Genetic Engineering of Ethanol Production in *Escherichia coli*" Appl. Environ Microbial 53: 2420–2425). A map of the pLOI295 plasmid is illustrated in FIG. 1. In particular, the DNA segment excised from the pLOI295 plasmid includes the pdc sequence starting at −46 bp (relative to the transcription start site) to a position +27 bp after the translation stop codon and is listed in EMBL as Accession No. M15393 and the DNA adh sequence starting from −31 bp up from the ATG initiation codon to +164 bp after the translation stop codon, which is listed in EMBL as Accession No. M15394.

EXAMPLE 1 pCB4-Rpa

The pCB4-Rpa construct is driven by a promoter obtained from the rbcLS operon of the cyanobacterium Synechococcus PCC 7942. The promoter sequence from the rbcLS operon was amplified from Synechococcus PCC 7942 by the polymerase chain reaction (PCR) using the forward primer identified as SEQ ID No. 1 (containing a BamHI site) and the reverse primer identified as SEQ ID No. 2 (containing an EcoRI site). These primers were designed according to the rbcL gene sequence obtained from the cyanobacterium *Anacystis nidulan* 6301, a strain genetically similar to Synechococcus PCC 7942. (Shinozaki K. et al. (1983) "Molecular cloning and sequence analysis of the Cyanobacteria gene for the large subunit of ribulose-1,5-bisphosphate carboxylase-oxygenase." Proc Natl Acad Sci USA 80:4050–4054). The PCR reaction mixture (100 $\mu$l) contained 0.5 $\mu$M of each primer, 0.4 mM dNTP, 10 ng genomic DNA from Synechococcus sp. PCC 7942 and 2 units of $Vent_R$ DNA plolymerase (New England Biolabs) in 1× reaction buffer: 10 mM KCl, 10 mM $(NH_4)_2SO_4$, 20 mM Tris-HCl (pH 8.8 at 25° C.), 2 mM $MgCl_2$ and 0.1% Triton X-100. PCR reactions were carried out in PTC-100TM Programmable Thermal Controller (MJ Research, Inc.) by using the temperature cycles as follows: 93° C./3 min; 30 cycles of 93° C./1 min, 62° C./1.5 min, 72° C./0.5 min; 72° C./5. The PCR product of expected size was cloned into the BamHI-EcoRI sites of the plasmid pBlueScript SK (Stratagene Inc.) to generate a plasmid designated pRBCp.

Figure 2:
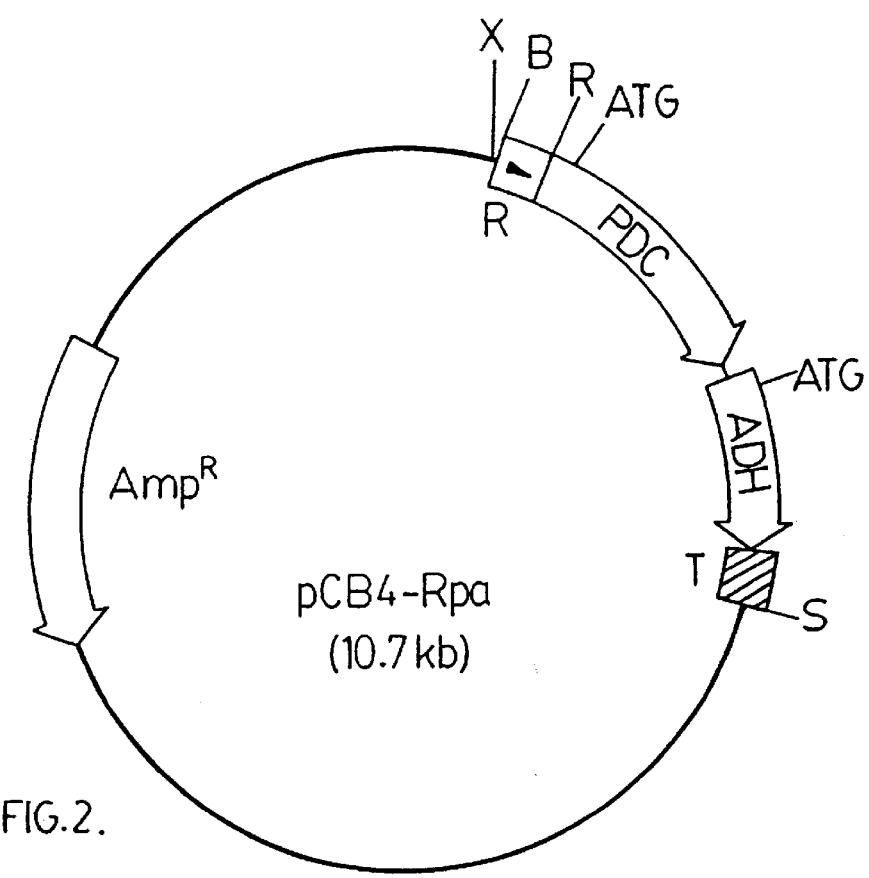
FIG. 2 is an illustration of the map of the plasmid construct pCB4-Rpa.

A 3.2 kbp EcoRI-SalI DNA fragment containing the pdc-adh sequence from *Zymomonas mobilis* was isolated from the pLOI295 plasmid and ligated into the corresponding sites of pRBCp to generate the plasmid pRpa. The pLOI295 plasmid map is illustrated in the map in FIG. 1. A 3.6 kbp BamHI DNA fragment containing the rbcLS promoter region and the pdc-adh sequences were then excised from pRpa and ligated into the BamHI site of the shuttle vector pCB4 (Gendel et al., (1983) "Shuttle Cloning Vectors for the Cyanobacterium *Anacystis Nidulans*", J. Bacteriol, 156: 148–154) resulting in the vector construct pCB4-Rpa. The shuttle vector pCB4 contains genes encoding ampicillan resistance. The vector construct pCB4-Rpa is illustrated in FIG. 2.

EXAMPLE 2 pCB4-LRpa

Figure 3:
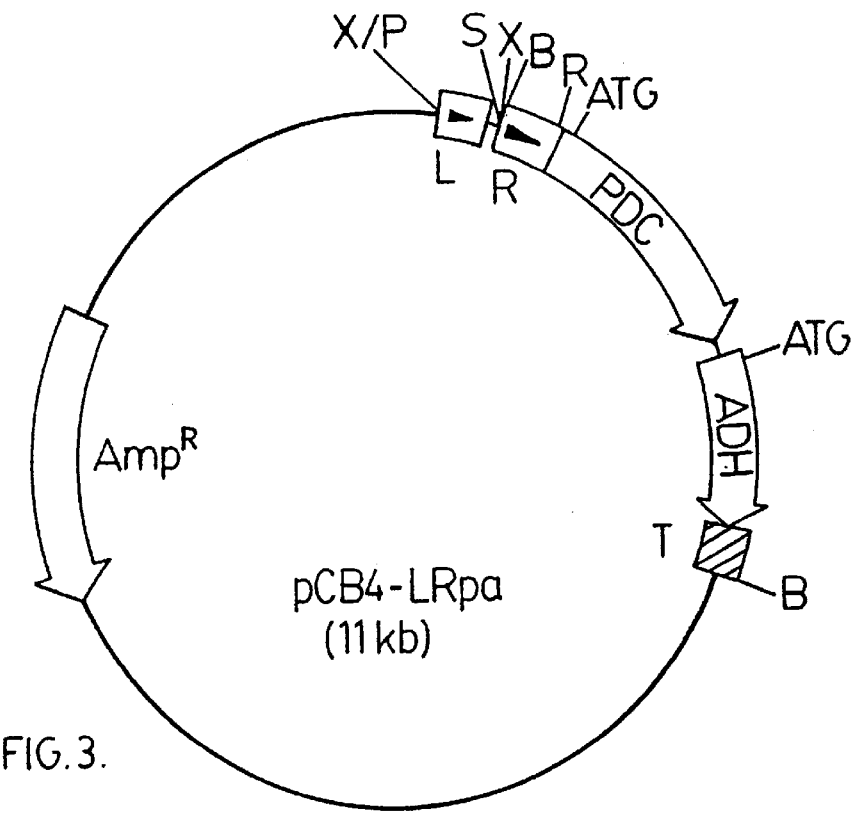
FIG. 3 is an illustration of the map of the plasmid construct pCB4-LRpa.

A 3.6 kbp BamHI DNA fragment from pRpa was ligated into a modified version of pCB4. The modified version of pCB4 is constructed by ligating a 220 bp PvuII-BamHI DNA fragment from the plasmid pBS (Stratagene Inc., 11011 North Torrey Pines Road, La Jolla, Calif., U.S.A. 92037), which fragment contains the lacZ promoter region from *Escherichia coli*, into the modified XbaI-BamHI sites of the pCB4 multi-cloning site. (Soltes-Rak E et al. (1993) "Effect of promoter modification on mosquitocidal cryIVB gene expression in Synechococcus sp. strain PCC 7942." Appl Environ Microbio. 59: 2404–2410). The 3.6 kbp DNA fragment is then ligated into the modified version of pCB4 resulting in the vector construct pCB4-LRpa. The vector construct pCB4-LRpa is illustrated in FIG. 3.

EXAMPLE 3 pCB4-LR(TF)pa

The pdc-adh coding region is driven by a combination of the rbcLS and lacZ promoter regions, as in pCB4-LRpa, but in this construct the *Zymomonas mobilis* pdc ribosome binding site and start codon have been removed and replaced with the corresponding DNA region of the rbcL sequence from Synechococcus PCC 7942 to generate a translation fusion product.

Figure 4:
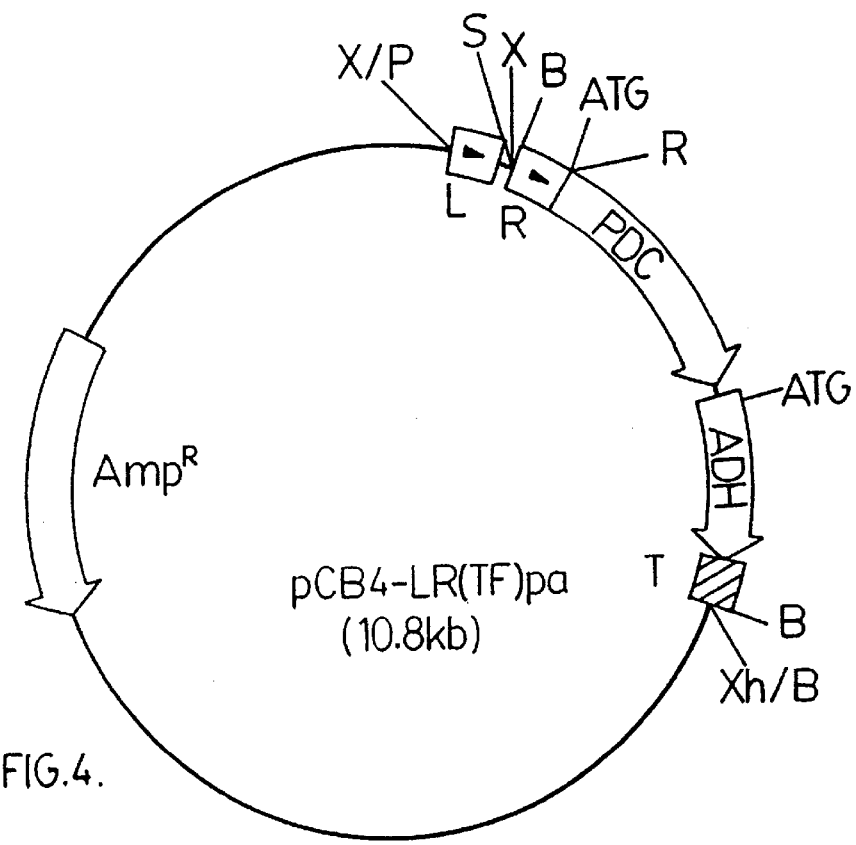
FIG. 4 is an illustration of the map of the plasmid construct pCB4-LR(TF)pa.
Figure 5:
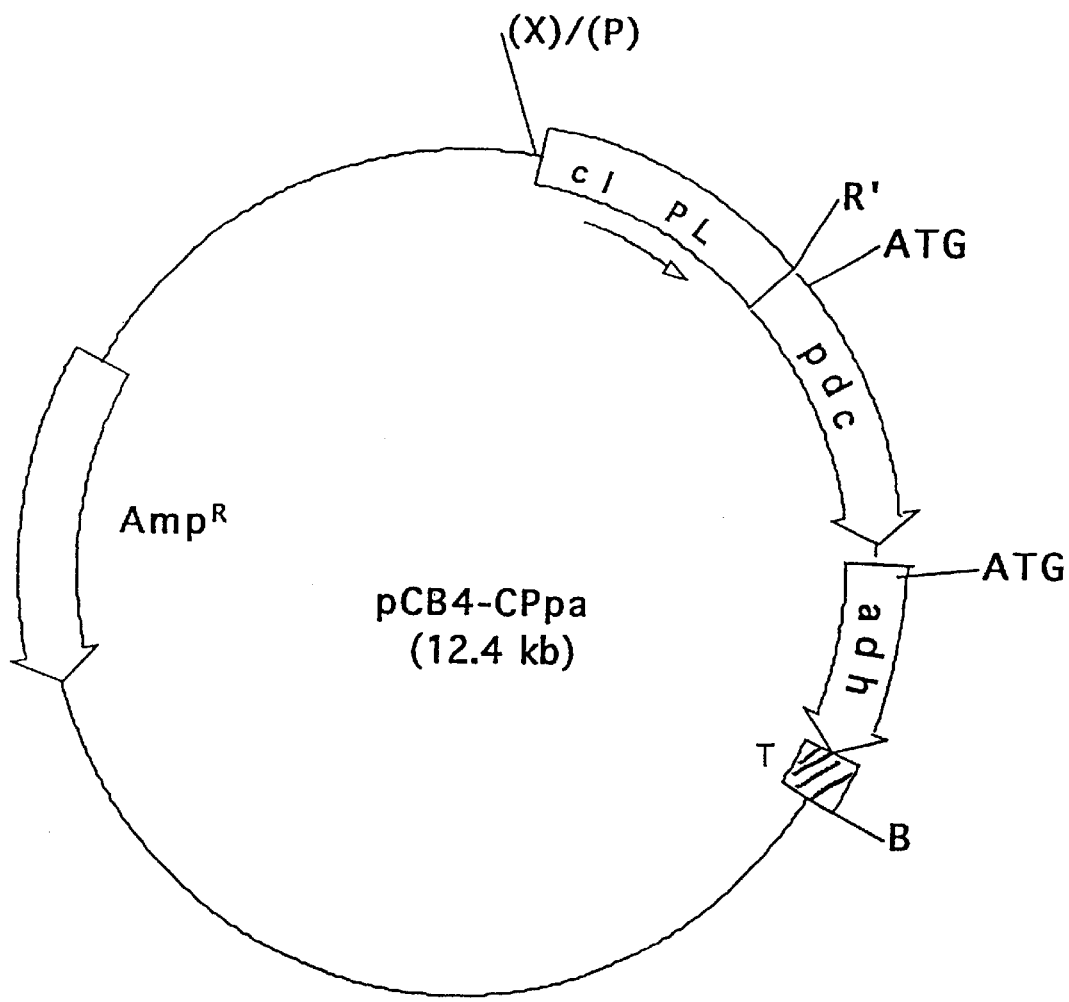
FIG. 5 is an illustration of the map of the plasmid construct pCB4-CPpa.

The pdc-adh DNA segment in pLOI295 plasmid is amplified and modified by PCR using the forward primer identified as SEQ ID No. 3 (containing an EcoRI site) and reverse primer identified as SEQ ID No. 4 (containing BamHI and XhoI sites). The PCR reaction mixture was as described above for Example 1. The temperature cycles were as follows: 93° C./5 min; 4 cycles of 93° C./1 min, 56° C./1.5 min, 72° C./3.5 min; 30 cycles of 93° C./1 min, 65° C./1.5° C., 72° C./3.5 min; 72° C./5 min. The 3.1 kbp PCR product was then ligated into pRBCp at the EcoRI-XhoI sites (double-cut) to generate plasmid pR(TF)pa (TF as in Translation Fusion). The cloning for translation fusion generated an extra codon AAT (asparagine) immediately after the initiation codon and the original second codon, AGT in pdc open reading frame was replaced by TCT to code the same amino acid (serine). This new plasmid was digested with XhoI, the cut sites blunt ended with Klenow fragment from DNA polI, and then digested with XbaI. This DNA fragment containing rbc-(TF)pdc-adh was then ligated into pCB4-lac which had been prepared by digestion with BamHI, blunt ended with Klenow, and redigested with XbaI. The resulting plasmid is designated pCB4-LR(TF)pa and is illustrated in FIG. 4.

EXAMPLE 4 pCB4-CPpa

The vector pCB4-Rpa was digested with XbaI, end-filled with Klenow fragment of DNA polymerase I and re-digested with EcoRI to delete the rbcLS promoter. The vector was then ligated to a PstI-EcoRI fragment containing the CI857 repressor gene and $P_L$ promoter sequence, collectively termed the cI-PL gene sequence (EMBL Accession No. L05669; Sanger et al. *Nucleotide sequence of the bacteriophage lambda DNA*. 1982, J. Mole. Biol. 162: 729–773) and identified as SEQ. ID. No. 7. The $P_L$ promoter had been isolated from the plasmid pHUB2-CI857 (Gruber et al. (1991)) "*Escherichia coli-Anacystis nidulans* plasmid shuttle vectors containing the $P_L$ promoter from bacteriophage lambda." Curr. Microbio. 22:15–19). The vector was litigated by digestion with PstI, end-filling with Klenow and a second digestion with EcoRI. The recombinant plasmid is designated as pCB4-CPpa.

EXAMPLE 5

Genetically Modified Synechococcus PCC 7942

Each of the four constructs of Examples 1, 2, 3 and 4 were incorporated into the Synechococcus PCC 7942.

The constructs of Examples 1, 2, 3 and 4 were incorporated into the Synechococcus PCC 7942 using a standard protocol as set out in Golden SS et al. (1987) "Genetic engineering of the Cyanobacteria chromosome" Methods Enzymol 153: 215–231 and in S. S. Golden and L. A. Sherman, J. Bacteriology 158:36 (1984), incorporated herein by reference. Briefly, cells of Synechococcus PCC 7942 are harvested by centrifugation and re-suspended in BG-11 medium at a concentration of $2–5 \times 10^8$ cells per ml. To one ml of this cell solution is added the appropriate plasmid construct DNA to a final concentration of 2 µg. ml$^{-1}$. Cells are incubated in the dark for 8 hours followed by a 16 h light incubation prior to plating on BG-11 plates containing 1 µg.ml$^{-1}$ ampicillin. Plates are incubated under the standard growth conditions (30° C. light intensity of 100 µmol photons. m$^{-2}$.s$^{-1}$). Ampicillin resistant colonies were visible in 7–10 days.

The genetically modified Synechococcus PCC 7942 were grown, bubbling with air at 30 and a light intensity of 100 µE.M$^{-2}$.s$^{-1}$ in liquid BG-11 medium containing 5 µg.ml$^{-1}$ ampicillin (Soltes-Rak E et al. (1993) "Effect of promoter modification on mosquitocidal cryIVB gene expression in Synechococcus sp. strain PCC 7942." Appl Environ Microbio. 59: 2404–2410) The activity of pdc, adh and the production of ethanol were measured as set out in Table 1 below for Examples 1, 2 and 3. The ethanol production for Example 3 is also illustrated in FIG. 8. Table 2 illustrates the ethanol production for Example 4. FIGS. 6 and 7 illustrate the pdc activity and adh expression, respectively, for Example 4. The activity of pdc was measured by determining the rate of pyruvic acid dependent reduction of NAD$^+$ with yeast with adh as the coupling enzyme as previously described in Conway et al., J. Bacteriology 169:2591–2597 (1987). Adh was measured for Examples 1, 2 and 3 by determining the rate of ethanol dependent NADH oxidation as described in Neale et al., Eur. J. Biochem. 154: 119–124 (1986). Ethanol was assayed using a standard Ethanol Assay kit obtained from Boehringer Mannheim Canada, Laval, Quebec. The results of the tests for pdc and adh activity and ethanol production for the constructs of Examples 1–3 are illustrated in Table 1.

TABLE 1

| Constructs | PDC Activity nmol.min.$^{-1}$.mg$^{-1}$ SP[1] | ADH Activity nmol.min.$^{-1}$.mg$^{-1}$ SP | Ethanol Conc. in medium (µM)[3] | Ethanol Conc. in µmoL.mg$^{-1}$ Chlorophyll |
|---|---|---|---|---|
| pCB4[4] | ND[2] | ND | ND | ND |
| pCB4-Rpa | 130 | 168 | 1370 | 274 |
| pCB4-LRpa | 136 | 168 | 1540 | 308 |
| pCB4-LR(TF)pa | 234 | 168 | 1710 | 342 |

[1]SP, soluble protein.
[2]ND, not detectable.
[3]Represents ethanol concentration in medium following 21 days growth in batch culture at a final cell density of OD$_{730}$1.5. This OD represents approximately $5 \times 10^8$ cells.ml$^{-1}$. Values in table are an underestimation of ethanol concentration as some ethanol is lost from the unsealed culture vessels during aeration. Concentrations approximating 5 mM can be achieved following 28 days of growth.
[4]Synechococcus PCC 7942 cells transformed with the shuttle vector pCB4 alone.

Synechococcus PCC 7942 cells were transformed with the vector pCB4-CPpa. The transformed cells were first grown at 30 degrees Celsius as set out above and then transferred to 42 degrees Celsius for 48 hours. Cells were harvested at intervals to assay pdc activity. As shown in FIG. 6, pdc activity was induced at 42 degrees, reaching a 20-fold increase at 48 hours after the temperature shift. Surprisingly, the pdc activity induced at 42 degrees Celsius with the pCB4-CPpa vector after 48 hours was approximately 2000 nmol.min.$^{-1}$.mg$^{-1}$ SP, which is about 20-fold higher than in the strain harboring the shuttle vector pCB4-Rpa which had a pdc activity of approximately 130 nmol.min.$^{-1}$mg$^{-1}$ SP as can be seen in FIG. 6 and Table 1, respectively.

The impact of temperature shift on ethanol synthesis was studied in liquid batch culture. The rate of ethanol synthesis at 42 degrees Celsius was 1.7 µmol ethanol per mg of chlorophyll per hour. As such, it was 5-times higher at 42 degrees than at 30 degrees Celsius, as can be seen in Table 2.

TABLE 2

Effect of temperature shift on Ethanol Synthesis
Synechococcus PCC 7942 cells transformed with the shuttle vector pCB4-CPpa were first grown at 30 deg. Celsius in the light, harvested at log phase and resuspended into a fresh medium at a cell density of 4.3 µg chlorophyll per ml. The resuspended cells were grown for 48 h in the light at 30 deg. Celsius and 42 deg. Celsius, respectively. The value in the brackets indicates the S.D. for 4 different samples.

| Temperature | Ethanol Conc. (µmol.mg$^{-1}$chlorophyll) | Rate of Ethanol Synthesis (µmol.mg$^{-1}$chlorophyll per hr) |
|---|---|---|
| 30 | 16(0.9) | 0.33 |
| 42 | 82(8.9) | 1.70 |

The above examples are intended to exemplify the invention. It is understood by the skilled workman in the art that various modifications and alterations may be made without departing from the scope of the invention and as set out in the claims attached hereto.

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

GCTGAATTCA TGTCGTCTCT CCCTAGAGA                        29

(2) INFORMATION FOR SEQ ID NO: 2:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 2:

GCTGAATTCA TGTCGTCTCT CCCTAGAGA                        29

(2) INFORMATION FOR SEQ ID NO: 3:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 3:

GGACTCGAGG ATCCCCAAAT GGCAA                           25

(2) INFORMATION FOR SEQ ID NO: 4:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 4:

GCATGAATTC TTATACTGTC GGTACCTAT                        29

(2) INFORMATION FOR SEQ ID NO: 5:

(i) SEQUENCE CHARACTERISTICS:
      (A) LENGTH: 1905 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 5:

-continued

```
TATCGCTCAT GATCGCGACA TGTTCTGATA TTTTCCTCTA AAAAAGATAA AAAGTCTTTT      60

CGCTTCGGCA GAAGAGGTTC ATCATGAACA AAAATTCGGC ATTTTTAAAA ATGCCTATA      120

CTAAATCCGG AACGACACTT TAGAGGTTTC TGGGTCATCC TGATTCAGAC ATAGTGTTT      180

GAATATATGG AGTAAGCAAT GAGTTATACT GTCGGTACCT ATTTAGCGGC GCTTGTCCA      240

ATTGGTCTCA AGCATCACTT CGCAGTCGCG GGCGACTACA ACCTCGTCCT TCTTGACAA      300

CTGCTTTTGA ACAAAAACAT GGAGCAGGTT TATTGCTGTA ACGAACTGAA CTGCGGTTT      360

AGTGCAGAAG GTTATGCTCG TGCCAAAGCG GACGCAGCAG CCGTCGTTAC CTACAGCGT      420

GGTGCGCTTT CCGCATTTGA TGCTATCGGT GGCGCCTATG CAGAAAACCT TCCGGTTAT      480

CTGATCTCCG GTGCTCCGAA CAACAATGAT CACGCTGCTG GTCACGTGTT GCATCACGC      540

CTTGGCAAAA CCGACTATCA CTATCAGTTG GAAATGGCCA AGAACATCAC GGCCGCAGC      600

GAAGCGATTT ACACCCCAGA AGAAGCTCCG GCTAAAATCG ATCACGTGAT TAAAACTGC      660

CTTCGTGAGA AGAAGCCGGT TTATCTCGAA ATCGCTTGCA ACATTGCTTC CATGCCCTG      720

GCCGCTCCTG GACCGGCAAG CGCATTGTTC AATGACGAAG CCAGCGACGA AGCTTCTTT      780

AATGCAGCGG TTGAAGAAAC CCTGAAATTC ATCGCCAACC GCGACAAAGT TGCCGTCCT      840

GTCGGCAGCA AGCTGCGCGC AGCTGGTGCT GAAGAAGCTG CTGTCAAATT TGCTGATGC      900

CTCGGTGGCG CAGTTGCTAC CATGGCTGCT GCAAAAAGCT TCTTCCAGAA GAAAACCGC      960

TTACATCGGT ACCTCATGGG TGAAGTCAGC TATCCGGGCG TTGAAAAGAC GATGAAAG     1020

GCCGATGCGG TTATCGCTCT GGCTCCTGTC TTCAACGACT ACTCCACCAC TGGTTGGA     1080

GATATTCCTG ATCCTAAGAA ACTGGTTCTC GCTGAACCGC GTTCTGTCGT CGTTAACG     1140

GTTCGCTTCC CCAGCGTTCA TCTGAAAGAC TATCTGACCC GTTTGGCTCA GAAAGTTT     1200

AAGAAAACCG GTGCTTTGGA CTTCTTCAAA TCCCTCAATG CAGGTGAACT GAAGAAAG     1260

GCTCCGGCTG ATCCGAGTGC TCCGTTGGTC AACGCAGAAA TCGCCCGTCA GGTCGAAG     1320

CTTCTGACCC CGAACACGAC GGTTATTGCT GAAACCGGTG ACTCTTGGTT CAATGCTC     1380

CGCATGAAGC TCCCGAACGG TGCTCGCGTT GAATATGAAA TGCAGTGGGG TCACATCG     1440

TGGTCCGTTC CTGCCGCCTT CGGTTATGCC GTCGGTGCTC CGGAACGTCG CAACATCC     1500

ATGGTTGGTG ATGGTTCCTT CCAGCTGACG GCTCAGGAAG TCGCTCAGAT GGTTCGCC     1560

AAACTGCCGG TTATCATCTT CTTGATCAAT AACTATGGTT ACACCATCGA AGTTATGA     1620

CATGATGGTC CGTACAACAA CATCAAGAAC TGGGATTATG CCGGTCTGAT GGAAGTGT     1680

AACGGTAACG GTGGTTATGA CAGCGGCGCT GGTAAAGGCC TGAAGGCTAA AACCGGTG     1740

GAACTGGCAG AAGCTATCAA GGTTGCTCTG GCAAACACCG ACGGCCCAAC CCTGATCG     1800

TGCTTCATCG GTCGTGAAGA CTGCACTGAA GAATTGGTCA AATGGGGTAA GCGCGTTG     1860

GCCCGCCAAC AGCCGTAAGC CTGTTAACAA GCTCCTCTAG TTTTT                   1905
```

(2) INFORMATION FOR SEQ ID NO: 6:

(i) SEQUENCE CHARACTERISTICS:
        (A) LENGTH: 1747 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

```
AAAGGCAAAA TCGGTAACCA CATCTCAATT ATTAAACAAT ACTTCATAAT AAAAAGACAA      60
```

-continued

```
CTTTTTCATA ATTTGCATAA GTCTTGATGT AAAAAATACA TATTTAGAAA GAACAAGCA       120

CCTTGCTCAT CACCGCTGTC GCGAGTAGAA AAATCTCGGC TTTCAGAAAA AGAGGCCGC       180

TCGTTAAACA GACTATAAAT GTGCTGGAAT AAAGCGAACC CCTTGATCTG ATAAAACTG       240

TAGACATATT GCTTTTGCGC TGCCCGATTG CTGAAAATGC GTAAAAGGTG ATTTTACTC       300

TTTTCAGGAA AAACTTTGAG AAAACGTCTC GAAAACGGGA TTAAAACGCA AAAACAATA       360

AAAGCGATTT CGCGAAAATG GTTGTTTTCG GGTTGTTGCT TTAAACTAGT ATGTAGGGT       420

AGGTTATAGC TATGGCTTCT TCAACTTTTT ATATTCCTTT CGTCAACGAA ATGGGCGAA       480

GTTCGCTTGA AAAAGCAATC AAGGATCTTA ACGGCAGCGG CTTTAAAAAT GCGCTGATC       540

TTTCTGATGC TTTCATGAAC AAATCCGGTG TTGTGAAGCA GGTTGCTGAC CTGTTGAAA       600

CACAGGGTAT TAATTCTGCT GTTTATGATG GCGTTATGCC GAACCCGACT GTTACCGCA       660

TTCTGGAAGG CCTTAAGATC CTGAAGGATA ACAATTCAGA CTTCGTCATC TCCCTCGGT       720

GTGGTTCTCC CCATGACTGC GCCAAAGCCA TCGCTCTGGT CGCAACCAAT GGTGGTGAA       780

TCAAAGACTA CGAAGGTATC GACAAATCTA AGAAACCTGC CCTGCCTTTG ATGTCAATC       840

ACACGACGGC TGGTACGGCT TCTGAAATGA CGCGTTTCTG CATCATCACT GATGAAGTC       900

GTCACGTTAA GATGGCCATT GTTGACCGTC ACGTTACCCC GATGGTTTCC GTCAACGAT       960

CTCTGTTGAT GGTTGGTATG CCAAAAGGCC TGACCGCCGC CACCGGTATG GATGCTCT       1020

CCCACGCATT TGAAGCTTAT TCTTCAACGG CAGCTACTCC GATCACCGAT GCTTGCGC       1080

TGAAGGCTGC GTCCATGATC GCTAAGAATC TGAAGACCGC TTGCGACAAC GGTAAGGA       1140

TGCCAGCTCG TGAAGCTATG GCTTATGCCC AATTCCTCGC TGGTATGGCC TTCAACAA       1200

CTTCGCTTGG TTATGTCCAT GCTATGGCTC ACCAGTTGGG CGGCTACTAC AACCTGCC       1260

ATGGTGTCTG CAACGCTGTT CTGCTTCCGC ATGTTCTGGC TTATAACGCC TCTGTCGT       1320

CTGGTCGTCT GAAAGACGTT GGTGTTGCTA TGGGTCTCGA TATCGCCAAT CTCGGTGA       1380

AAGAAGGCGC AGAAGCCACC ATTCAGGCTG TTCGCGATCT GGCTGCTTCC ATTGGTAT       1440

CAGCAAATCT GACCGAGCTG GGTGCTAAGA AGAAGATGT GCCGCTTCTT GCTGACCA       1500

CTCTGAAAGA TGCTTGTGCT CTGACCAACC CGCGTCAGGG TGATCAGAAA GAAGTTGA       1560

AACTCTTCCT GAGCGCTTTC TAATTTCAAA ACAGGAAAAC GGTTTTCCGT CCTGTCTT       1620

TTTTCAAGCA AACAATGCCT CCGATTTCTA ATCGGAGGCA TTTGTTTTTG TTTATTGC       1680

AAACAAAAAA TATTGTTACA AATTTTTACA GGCTATTAAG CCTACCGTCA TAAATAAT       1740

GCCATTT                                                              1747
```

(2) INFORMATION FOR SEQ ID NO: 7:

(i) SEQUENCE CHARACTERISTICS:
  (A) LENGTH: 7922 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO: 7:

```
GGCGGAGTAA AAAGAGGAGC CCGGCGTCAT CTTTTGTTAC CCGCCAAACA AACCCAAAA       60

ACAACCCATA CCCAAGCCAA TAAAACACCA AACAAGACA AATAATCATT GATTGATGG       120

TGAAATGGGG TAAACTTGAC AAACAAACCC ACTTAAAACC CAAAACATAC CCAAACACA       180

ACCAAAAAAA CACCATAAGG AGTTTTATAA ATGTTGGTAT TCATTGATGA CGGTTCAAC       240
```

-continued

```
AACATCAAAC TACAGTGGCA GGAAAGCGAC GGAACAATTA ACAGCACAT TAGCCCGAA      300
AGCTTCAAAC GCGAGTGGGC AGTCCCTTTT GGTGATAAAA AGGTCTTTAA CTACACACT      360
AACGGCGAAC AGTATTCATT TGATCCAACC AGCCCGGATG CTGTAGTCAC AACCAATAT      420
GCATGGCAAT ACAGCGACGT TAATGTCGTT GCAGTGCATC ACGCCTTACT GACCAGTGG      480
CTGCCGGTAA GCGAAGTGGA TATTGTTTGC ACACTTCCTC TGACAGAGTA TTACGACAG      540
AATAACCAAC CCAATACGGA AAATATTGAG CGTAAGAAAG CAAACTTCCG GAAAAAAAT      600
ACATTAAATG GCGGGATAC ATTCACAATA AAAGATGTAA AAGTCATGCC TGAATCTAT       660
CCGGCAGGTT ATGAAGTTCT ACAAGAACTG GATGAGTTAG ATTCTTTATT AATTATAGA      720
CTCGGGGCA CCACATTAGA TATTTCTCAG GTAATGGGGA AATTATCGGG GATCAGTAA       780
ATATACGGAG ACTCATCTCT TGGTGTCTCT CTGGTTACAT CTGCAGTAAA AGATGCCCT      840
TCTCTTGCGA GAACAAAAGG AAGTAGCTAT CTTGCTGACG ATATAATCAT TCACAGAAA      900
GATAATAACT ATCTGAAGCA ACGAATTAAT GATGAGAACA AAATATCAAT AGTCACCGA      960
GCAATGAATG AAGCACTTCG TAAACTTGAG CAACGTGTAT TAAATACGCT CAATGAAT       1020
TCTGGTTATA CTCATGTTAT GGTTATAGGC GGTGGCGCAG AATTAATATG CGATGCAG       1080
AAAAAACACA CACAGATTCG TGATGAACGT TTTTTCAAAA CCAATAACTC TCAATATG       1140
TTAGTTAACG GTATGTATCT CATAGGTAAT TAATGATGGA CAAGCGCAGA ACCATTGC       1200
TCAAACTAAA TCCAGATGTA AATCAAACAG ATAAAATTGT TTGTGATACA CTGGACAG       1260
TCCCGCAAGG GGAACGAAGC CGCCTTAACC GGGCCGCACT GACGGCAGGT CTGGCCTT       1320
ACAGACAAGA TCCCCGGACC CCTTTCCTTT TATGTGAGCT GCTGACGAAA GAAACCAC       1380
TTTCAGATAT CGTGAATATA TTGAGATCGC TATTTCCAAA AGAGATGGCC GATTTTAA       1440
CTTCAATAGT CACTCAATCC TCTTCACAAC AAGAGCAAAA AAGTGATGAA GAGACCAA       1500
AAAATGCGAC GAAGCTAATA AAATTAATTC AATTATTATT GAGTTCCCTT TATCCACT       1560
CAGGCTGGAT AAAGGGAACT CAATCAAGTT ATTTTCTTAC CAGTCATTAC ATAATCGT       1620
TTATGAAATA ATCGTTTGCA CTGTCTCTGT TATTCAGGCA ATTTCAATAA AGGCACTT       1680
TCACGCTCTG TCATTTTCTG AAACTCTTCA TGCTGCATTT CGCAGGTGGC ACTTTTCG       1740
GAAATGTGCG CGGAACCCCT ATTTGTTTAT TTTTCTAAAT ACATTCAAAT ATGTATCC       1800
TCATGAGACA ATAACCCTGA TAAATGCTTC AATAATATTG AAAAAGGAAG AGTATGAG       1860
TTCAACATTT CCGTGTCGCC CTTATTCCCT TTTTTGCGGC ATTTTGCCTT CCTGTTTT       1920
CTCACCCAGA AACGCTGGTG AAAGTAAAAG ATGCTGAAGA TCAGTTGGGT GCACGAGT       1980
GTTACATCGA ACTGGATCTC AACAGCGGTA AGATCCTTGA GAGTTTTCGC CCCGAAGA       2040
GTTTTCCAAT GATGAGCACT TTTAAAGTTC TGCTATGTGG CGCGGTATTA TCCCGTGT       2100
ACGCCGGGCA AGAGCAACTC GGTCGCCGCA TACACTATTC TCAGAATGAC TTGGTTGA       2160
ACTCACCAGT CACAGAAAAG CATCTTACGG ATGGCATGAC AGTAAGAGAA TTATGCAG       2220
CTGCCATAAC CATGAGTGAT AACACTGCGG CCAACTTACT TCTGACAACG ATCGGAGG       2280
CGAAGGAGCT AACCGCTTTT TTGCACAACA TGGGGGATCA TGTAACTCGC CTTGATCG       2340
GGGAACCGGA GCTGAATGAA GCCATACCAA ACGACGAGCG TGACACCACG ATGCCTGC       2400
CAATGGCAAC AACGTTGCGC AAACTATTAA CTGGCGAACT ACTTACTCTA GCTTCCCG       2460
AACAATTAAT AGACTGGATG GAGGCGGATA AAGTTGCAGG ACCACTTCTG CGCTCGGC       2520
TTCCGGCTGG CTGGTTTATT GCTGATAAAT CTGGAGCCGG TGAGCGTGGG TCTCGCGG       2580
```

-continued

```
TCATTGCAGC ACTGGGGCCA GATGGTAAGC CCTCCCGTAT CGTAGTTATC TACACGAC      2640

GGAGTCAGGC AACTATGGAT GAACGAAATA GACAGATCGC TGAGATAGGT GCCTCACT      2700

TTAAGCATTG GTAACTGTCA GACCAAGTTT ACTCATATAT ACTTTAGATT GATTTAGC      2760

GAATTAATTC CCGGAAGAGA GTCAATTCAG GGTGGTGAAT ATGAAACCAG TAACGTTA      2820

CGATGTCGCA GAGTATGCCG GTGTCTCTTA TCAGACCGTT TCCCGCGTGG TGAACCAG      2880

CAGCCACGTT TCTGCGAAAA CGCGGGAAAA AGTGGAAGCG GCGATGGCGG AGCTGAAT      2940

CATTCCCAAC CGCGTGGCAC AACAACTGGC GGGCAAACAG TCGTTGCTGA TTGGCGTT      3000

CACCTCCAGT CTGGCCCTGC ACGCGCCGTC GCAAATTGTC GCGGCGATTA AATCTCGC      3060

CGATCAACTG GGTGCCAGCG TGGTGGTGTC GATGGTAGAA CGAAGCGGCG TCGAAGCC      3120

TAAAGCGGCG GTGCACAATC TTCTCGCGCA ACGCGTCAGT GGGCTGATCA TTAACTAT      3180

GCTGGATGAC CAGGATGCCA TTGCTGTGGA AGCTGCCTGC ACTAATGTTC CGGCGTTA      3240

TCTTGATGTC TCTGACCAGA CACCCATCAA CAGTATTATT TTCTCCCATG AAGACGGT      3300

GCGACTGGGC GTGGAGCATC TGGTCGCATT GGGTCACCAG CAAATCGCGC TGTTAGCG      3360

CCCATTAAGT TCTGTCTCGG CGCGTCTGCG TCTGGCTGGC TGGCATAAAT ATCTCACT      3420

CAATCAAATT CAGCCGATAG CGGAACGGGA AGGCGACTGG AGTGCCATGT CCGGTTTT      3480

ACAAACCATG CAAATGCTGA ATGAGGGCAT CGTTCCCACT GCGATGCTGG TTGCCAAC      3540

TCAGATGGCG CTGGGCGCAA TGCGCGCCAT TACCGAGTCC GGGCTGCGCG TTGGTGCG      3600

TATCTCGGTA GTGGGATACG ACGATACCGA AGACAGCTCA TGTTATATCC CGCCGTCA      3660

CACCATCAAA CAGGATTTTC GCCTGCTGGG GCAAACCAGC GTGGACCGCT TGCTGCAA      3720

CTCTCAGGGC CAGGCGGTGA AGGGCAATCA GCTGTTGCCC GTCTCACTGG TGAAAAGA      3780

AACCACCCTG GCGCCCAATA CGCAAACCGC CTCTCCCCGC GCGTTGGCCG ATTCATTA      3840

GCAGCTGGCA CGACAGGTTT CCCGACTGGA AAGCGGGCAG TGAGCGCAAC GCAATTAA      3900

TCGAAAAACT TCATTTTTAA TTTAAAAGGA TCTAGGTGAA GATCCTTTTT GATAATCT      3960

TGACCAAAAT CCCTTAACGT GAGTTTTCGT TCCACTGAGC GTCAGACCCC GTAATAAG      4020

GATCTTCTTG AGATCGTTTT GGTCTGCGCG TAATCTCTTG CTCTGAAAAC GAAAAAAC      4080

CCTTGCAGGG CGGTTTTTCG TATGATACAG GAGTAAAACC GCCGAAGCCC GGCGTAAG      4140

GGTACTGATT GATAGATTTC ACCTTACCCA TCCCCAGCCC TGCCAGACCA TACCCGCT      4200

CAGCCATGAG AGAGCTTCTG TGCGCGGTCG GAGTGGTCCC GACGAGGGTT TACCCGAA      4260

CGGGGCGTGT CTCCGCGTTA GCGGGCCGTG AGGGCCGCTT ACGAGCGTGT ACTGAGAA      4320

TCCAGCGAGA AGACTGACAG CGATGAAGAT GTAGTTACAA CATTCATAAT TAAAAGCG      4380

TCTGTTCCGG CCCTTTGGGC CGGGGCGGGG CCGCTTTTCA GTTATGAGGG AGGGGCTT      4440

TGGTTTCGGT TCTGCGCTGG ACCGGGGTTT TCTGGAGGT TGTTTTTGTG TGTTGTAA      4500

AAAGTGGCTC CGGTCGGGGC CCGCCGCTTG CGGTGGGAGG TGCATATCTG TCTGTCCA      4560

GGACAGGCAG TGAATAGGTT TTCTTTTTAA ATGAATGTAA TTAAGTAGTT TAAAGGAG      4620

ATAAACAGGT GTTTAAAAGA TACATTGCAC CCTGTAAGAC TGGCGGCTGG CGCTTTAT      4680

CATGAACGGT TGTAACCTTA TGGGAAGTC CCTTGCAGTT AAATGTGGAT AAGCAAAA      4740

CCCCGTCGCT GAGGCGTATT TGTATTAAA AACAGGGGGA ATCGGATGCT CCAGAAGG      4800

GATGATGAGA TTGTTTTTTG CATGCGACGC TGTTTTTTTG TGCACCGGCG GCTTCAG      4860

GTGCGGATGC CTCCGGCGCA GGCCGGATTA TTCTGAGGAG ATCACTTTCA GGGAGAAG      4920

GTGGCCAGCC GGCTGTAATT GCGGTTACGT GACAGAATCA TGCGCTCCTT CACACGAC      4980
```

```
TCCACTTCGC GTTTTACCGC CTCACCATTA GCAGTGAAGC GTCCTTCCGA GATTTCAC     5040

GTCAGCTGCC GTTTCACTAG GGTGACGATA TCCTGACGTT CTCTGTTCGC ATCACGAC     5100

GCACGGGCAC GTTTTATTCC ACGGGACTGA AGCTCTGTCT GGTAACTGCG GAAACGCT     5160

CGCACAAAAC GCCAGGCTTT CGCTATCAGC TCATCCATAC CCAGGGTATC CAGCCCCT     5220

TTTTTGCGCT GTTTGTTTTC CCATTCAACA CGACTGCGGC GCGCAGCTGC CACTGCAT     5280

TCAGACACAT CAAGGGCAGC AAACAGAGCC AGTGTGAACG TGATGTCGGT CGGAATGT     5340

CACCCGATAA GCGGGTCATA TTCCGTCTGG TAGGTAATCA GTCCCAGCTC TGACAGGA     5400

GTCAGGGCCC GGGTGGCACG GGTGATGGAG AGTTTTCCTG CACCGGACTC TGTCGCCA     5460

CCGCACTCAA TGGCCAGTGT GGTGATGGAA CACTGGACGG GGTTGGCCAG CGGGTCAT     5520

TGGAAACACA GCCCCTGCAG CAGCGCATCA ATAGCCCGTC GACGCAGCAC CGGTGGCA     5580

CGCCGACGCA GACCACGGGA ACGGGCATGC GCCACATGAA TGGCGAAATC AAAACGGG     5640

GTGAGGCCCA CCGCCTTTTC CATCGGTTTT TCGCGGAACT TCGGCGTTCC GGCACCTT     5700

CGGGGAGTGA ACACCGGATT CGGGTTCTTT ACCTGGCGGT AATACGTTTG GTGAAGAT     5760

GTCACACCAT CCTGCACTTA CAATGCGCAG AAGGAGCGAG CACAGAAAGA AGTCTTGA     5820

TTTTCCGGGC ATATAACTAT ACTCCCCGCA TAGCTGAATT GTTGGCTATA CGGTTTAA     5880

GGGCCCCGGT AATCTTTTCG TACTCGCCAA AGTTGAAGAA GATTATCGGG TTTTTGC      5940

TTCTGGCTCC TGTAAATCCA CATCAGAACC AGTTCCTTGC CACCTTACGG CGTGGCAG     6000

ACAAAATTCC TTAAACGATC AGTAATCTAG CTAGCTACGC CACAAAGTAA AGTCTTTT     6060

TTTAGTATAT CCAGTCTCTG CAGTTCATCT TTGATGATTT TCTCAACGAA CTGAGCCT     6120

GTTATCCCCT CTCTCTCGCA GTACTCAACC ATGAGATCGA TCTTTCAGAG GATTTTTG     6180

AAAAACTTTT ATCTCTTTGT GTGTAAGACG TTTTCTTGCA ACAGCGGCCA TTTGTTTC     6240

AGAGTCAGTC ATAGGCTTAC CTCTGCGCAC AAACCGCTTT TGACTCAATG AGGAAGTC     6300

TGCATTTTCT GTCTGCGACA TCTCGCCTCC TCAATACTCA AACAGGGATC GTTTCGCA     6360

GGATACTACA GTTTTTTGAA ATCAGCAACT TGAGAATTGT GACGAAGATC TTTAGCTG     6420

TTGGTTTGCC CAAAGCGCAT TGCATAATCT TTCAGGGTTA TGCGTTGTTC CATACAAC     6480

CCTTAGTACA TGCAACCATT ATCACCGCCA GAGGTAAAAT AGTCAACACG CACGGTGT     6540

GATATTTATC CCTTGCGGTG ATAGATTTAA CGTATGAGCA CAAAAAAGAA ACCATTAA     6600

CAAGAGCAGC TTGAGGACGC ACGTCGCCTT AAAGCAATTT ATGAAAAAAA GAAAAATG     6660

CTTGGCTTAT CCCAGGAATC TGTCGCAGAC AAGATGGGGA TGGGGCAGTC AGGCGTTG     6720

GCTTTATTTA ATGGCATCAA TGCATTAAAT GCTTATAACG CCGCATTGCT TACAAAAA     6780

CTCAAAGTTA GCGTTGAAGA ATTTAGCCCT TCAATCGCCA GAGAAATCTA CGAGATGT     6840

GAAGCGGTTA GTATGCAGCC GTCACTTAGA AGTGAGTATG AGTACCCTGT TTTTTCTC     6900

GTTCAGGCAG GGATGTTCTC ACCTAAGCTT AGAACCTTTA CCAAAGGTGA TGCGGAGA     6960

TGGGTAAGCA CAACCAAAAA AGCCAGTGAT TCTGCATTCT GGCTTGAGGT TGAAGGTA     7020

TCCATGACCG CACCAACAGG CTCCAAGCCA AGCTTTCCTG ACGGAATGTT AATTCTCG     7080

GACCCTGAGC AGGCTGTTGA GCCAGGTGAT TTCTGCATAG CCAGCTTGG GGGTGATG      7140

TTTACCTTCA AGAAACTGAT CAGGGATAGC GGTCAGGTGT TTTTACAACC ACTAAACC     7200

CAGTACCCAA TGATCCCATG CAATGAGAGT TGTTCCGTTG TGGGGAAAGT TATCGCTA     7260

CAGTGGCCTG AAGAGACGTT TGGCTGATCG GCAAGGTGTT CTGGTCGGCG CATAGCTG     7320
```

-continued

| | | | | | |
|---|---|---|---|---|---|
| AACAATTGAG | CAAGAATCTT | CATCGAATTA | GGGGAATTTT | CACTCCCCTC | AGAACATA 7380 |
| ATAGTAAATG | GATTGAATTA | TGAAGAATGG | TTTTTATGCG | ACTTACCGCA | GCAAAAAT 7440 |
| AGGGAAAGAT | AAGCCTAGTG | CTACTTGAGG | GTATACCGCA | AGAATATACG | CAAGCGTC 7500 |
| GATAGCTGCC | AAAGCCGCAA | GGAATTTACC | AACCTTCTTA | AACATAAAGT | GTCTCCTT 7560 |
| AAACGCAGAA | AGGCCCACCC | GAAGGTGAGC | CAGTGTGATT | ACATTTTCTC | TTGAGGGT 7620 |
| TCCTCGGTGC | CACGGAACAT | TACGAACGAT | GGGTGCCGCA | AAGAGCCATC | AGGTGTTT 7680 |
| TCCATGTAGC | TAATTTGACA | CGCCCAGCCA | TCGTAAGGGT | TAATAGTAAT | TCGAGCTC 7740 |
| TACCCGGGGA | TCCTCTAGAG | CTCGAGGCCT | CATATGGATC | CACGTGAATT | CGTAATCA 7800 |
| TCATAGCTGT | TTCCTGTGTG | AAATTGTTAT | CCGCTCACAA | TTCCACACAA | CATACGAG 7860 |
| GGAAGCATAA | AGTGTAAAGC | CTGGGGTGCC | TAATGAGTGA | GCTAACTCAC | ATTACTAG 7920 |
| TC | | | | | 7922 |

We claim:

1. A process for producing ethanol which comprises the steps of: culturing in a culture medium Cyanobacteria and providing said Cyanobacteria with a source of carbon, said Cyanobacteria containing a construct comprising DNA fragments encoding pyruvate decarboxylase and alcohol dehydrogenase enzymes obtained from the *Zymomonas mobilis* pLOI295 plasmid; accumulating ethanol in the culture medium in an amount of approximately 1.7 μmol of ethanol per mg of chlorophyll per hour; and isolating the accumulated ethanol.

2. A process for producing ethanol according to claim 1 wherein said Cyanobacteria are Synechococcus and said construct is selected from the group consisting of pCB4-Rpa, pCB4-LRpa and pCB4-LR(TF)pa.

3. A process for producing ethanol according to claim 1 steps wherein said construct further comprises a DNA fragment comprising a temperature inducible gene and wherein said process comprises the further step of: increasing the temperature to a temperature which induces the expression of the pyruvate decarboxylase and alcohol dehydrogenase genes.

4. A process for producing ethanol according to claim 3 wherein said construct comprises temperature inducible gene CI857.

5. A process for producing ethanol according to claim 1 wherein said construct further comprises an rbcLS promoter of Synechococcus and a lacZ promoter of *Escherichia coli* operatively linked to said DNA fragments encoding pyruvate decarboxylase and alcohol dehydrogenase enzymes.

6. A process for producing ethanol according to claim 1 wherein the DNA fragment encoding the pyruvate decarboxylase enzyme is SEQ ID.NO.5.

7. A process for producing ethanol according to claim 1 wherein said DNA fragments encoding the alcohol dehydrogenase enzyme is SEQ ID NO.6.

8. A process for producing ethanol according to claim 1 wherein said Cyanobacteria are produced according to the following steps:
   a. selecting an appropriate promoter;
   b. ligating said promoter to pyruvate decarboxylase and alcohol dehydrogenase enzyme encoding DNA sequences;
   c. cloning said ligated sequences comprising said promoter, pyruvate decarboxylase and alcohol dehydrogenase sequences into an appropriate construct;
   d. transforming said construct into said Cyanobacteria.

9. A process for producing ethanol according to claim 1 wherein said Cyanobacteria are Synechococcus and said construct is pCB4-CPpa.

10. A process for producing ethanol according to claim 1 wherein said Cyanobacteria are Synechococcus PCC 7942.

* * * * *